US009623242B2

(12) United States Patent
Richter et al.

(10) Patent No.: US 9,623,242 B2
(45) Date of Patent: Apr. 18, 2017

(54) METHODS OF FREQUENCY-MODULATED PHASE CODING (FMPC) FOR COCHLEAR IMPLANTS AND COCHLEAR IMPLANTS APPLYING SAME

(71) Applicants: NORTHWESTERN UNIVERSITY, Evanston, IL (US); RESONANCE MEDICAL, LLC, Evanston, IL (US)

(72) Inventors: Claus-Peter Richter, Skokie, IL (US); Reagan Roberts, Chicago, IL (US)

(73) Assignees: NORTHWESTERN UNIVERSITY, Evanston, IL (US); RESONANCE MEDICAL, LLC, Chicago, IL (US)

( * ) Notice: Subject to any disclaimer, the term of this patent is extended or adjusted under 35 U.S.C. 154(b) by 0 days.

(21) Appl. No.: 15/206,921

(22) Filed: Jul. 11, 2016

(65) Prior Publication Data

US 2017/0007833 A1    Jan. 12, 2017

Related U.S. Application Data

(60) Provisional application No. 62/191,084, filed on Jul. 10, 2015, provisional application No. 62/320,132, filed on Apr. 8, 2016.

(51) Int. Cl.
  *A61N 1/36* (2006.01)
  *A61N 1/05* (2006.01)

(52) U.S. Cl.
  CPC ....... *A61N 1/36032* (2013.01); *A61N 1/0541* (2013.01)

(58) Field of Classification Search
  CPC .......................... A61N 1/36032; A61N 1/0541
  See application file for complete search history.

(56) References Cited

U.S. PATENT DOCUMENTS

| 4,593,696 A | 6/1986 | Hochmair et al. |
| 5,023,783 A | 6/1991 | Cohen et al. |

(Continued)

FOREIGN PATENT DOCUMENTS

| EP | 0441936 B1 | 12/1996 |
| WO | 0217678 A1 | 2/2002 |
| WO | 2014035854 A1 | 3/2014 |

OTHER PUBLICATIONS

McDermott, H.J. and A.E. Vandali, Spectral maxima sound processor. 1997, Google Patents.

(Continued)

*Primary Examiner* — Amanda Patton
(74) *Attorney, Agent, or Firm* — Locke Lord LLP; Tim Tingkang Xia, Esq.

(57) ABSTRACT

A method of generating frequency-modulated pulse trains in a CI includes dividing data representing audio spanning frequency bands into a plurality of bins associated with each frequency band, each bin representing an energy level of the data within the frequency band within a period of time; associating each frequency band with a phase probability that starts at an initial phase probability value (PPV), resets to a minimum PPV after generating a pulse, and increases from the minimum PPV to a maximum PPV over a period of time; for each bin, assigning a power probability as a normalized intensity being a number between a minimum power probability and a maximum power probability representing the energy level of the bin, and generating a pulse in an electrode associated with the frequency band associated with the bin when a random number generated is less than the power probability divided by the phase probability.

15 Claims, 27 Drawing Sheets

(56) References Cited

U.S. PATENT DOCUMENTS

| | | | |
|---|---|---|---|
| 7,171,272 | B2 | 1/2007 | Blamey et al. |
| 7,310,558 | B2 | 12/2007 | Van Hoesel |
| 8,019,431 | B2 | 9/2011 | Nie et al. |
| 8,185,383 | B2 | 5/2012 | Zeng et al. |
| 2004/0204659 | A1 | 10/2004 | John et al. |
| 2007/0203535 | A1 | 8/2007 | Zeng et al. |
| 2007/0239227 | A1* | 10/2007 | Fridman ............ A61N 1/36032 607/57 |
| 2010/0179616 | A1 | 7/2010 | Fridman et al. |

OTHER PUBLICATIONS

Killian, M., E Von Wallenberg, and G. Smoorenburg, Pulse burst electrical stimulation of nerve or tissue fibers. 2008, Google Patents.

Nolfe, J. and E. Schafer, Programming cochlear implants. 2014: Plural Publishing.

Chen, F and Y.-H. Lai, Modeling speech intelligibility with recovered envelope from temporal fine structure stimulus. Speech Communication, 2016. 81: p. 120-128.

Zeng, F.G., et al., On the dichotomy in auditory perception between temporal envelope and tine structure cues. J Acoust Soc Am, 2004. 116(3): p. 1351-4.

Rose, J.E., et al., Some effects of stimulus intensity on response of auditory nerve fibers in the squirrel monkey. J Neurophysiol, 1971. 34(4): p. 685-99.

Anderson, D.J., et al., Temporal position of discharges in single auditory nerve fibers within the cycle of a sine-wave stimulus: frequency and intensity effects. J Acoust Soc Am, 1971. 49(4): p. Suppl 2:1131-1139.

Brugge, J.F., et al., Time structure of discharges in single auditory nerve fibers of the squirrel monkey in response to complex periodic sounds. J Neurophysiol, 1969. 32(3): p. 386-401.

Kiang, N.Y., E.C. Moxon, and R.A. Levine, Auditory-nerve activity in cats with normal and abnormal cochleas. In: Sensorineural hearing loss. Ciba Found Symp, 1970: p. 241-73.

Kiang, N.Y., et al., Stimulus coding in the cat's auditory nerve. Preliminary report. Ann Otol Rhinol Laryngol, 1962. 71: p. 1009-26.

Liberman, M.C., Single-neuron labeling in the cat auditory nerve. Science, 1982. 216(4551): p. 1239-41.

Tasaki, I., Nerve impulses in individual auditory nerve fibers in guinea pig. J. Neurophysiol., 1954(17): p. 97-122.

Winter, P. and H.H. Funkenstein, The effect of species-specific vocalization on the discharge of auditory cortical cells in the awake squirrel monkey. (*Saimiri sciureus*). Exp Brain Res, 1973. 18(5): p. 489-504.

Newman, J.D. and Z. Wollberg, Responses of single neurons in the auditory cortex of squirrel monkeys to variants of a single call type. Exp Neurol, 1973. 40(3): p. 821-4.

Newman, J.D. and Z. Wollberg, Multiple coding of species-specific vocalizations in the auditory cortex of squirrel monkeys. Brain Res, 1973. 54: p. 287-304.

Delgutte, B., Speech coding in the auditory nerve: II. Processing schemes for vowel-like sounds. J Acoust Soc Am, 1984. 75(3): p. 879-86.

Delgutte, B. and N.Y. Kiang, Speech coding in the auditory nerve: IV. Sounds with consonant-like dynamic characteristics. J Acoust Soc Am, 1984. 75(3): p. 897-907.

Delgutte, B. and N.Y. Kiang, Speech coding in the auditory nerve: III. Voiceless fricative consonants. J Acoust Soc Am, 1984. 75(3): p. 887-96.

Delgutte, B. and N.Y. Kiang, Speech coding in the auditory nerve: I. Vowel-like sounds. J Acoust Soc Am, 1984. 75(3): p. 866-78.

Miller, R.L., B.M. Calhoun, and E.D. Young, Discriminability of vowel representations in cat auditory-nerve fibers after acoustic trauma. J Acoust Soc Am, 1999. 105(1): p. 311-25.

Richter, C.P., S. Heynert, and R. Klinke, Rate-intensity-functions of pigeon auditory primary afferents. Hear Res, 1995. 33(1-2): p. 19-25.

Yates, G.K., G.A. Manley, and C. Koppl, Rate-intensity functions in the emu auditory nerve. J Acoust Soc Am, 2000. 107(4): p. 2143-54.

Koppl, C. and G. Yates, Coding of sound pressure level in the barn owl's auditory nerve. J Neurosci, 1999. 19(21): p. 9674-86.

Yates, G.K., Basilar membrane nonlinearity and its influence on auditory nerve rate-intensity functions. Hear Res, 1990. 50(1-2): p. 145-62.

Yates, G.K., I.M. Winter, and D. Robertson, Basilar membrane nonlinearity determines auditory nerve rate-intensity functions and cochlear dynamic range. Hear Res, 1990. 45(3): p. 203-19.

Winter, I.M., D. Robertson, and G.K. Yates, Diversity of characteristic frequency rate-intensity functions in guinea pig auditory nerve fibres. Hear Res, 1990. 45(3): p. 191-202.

Burns, E.M., Developing a Catholic health care system. Hosp Prog, 1976. 57(12): p. 48-54, 80.

Dorman, M.F., P.C. Loizou, and D. Rainey, Speech intelligibility as a function of the Number of channels of stimulation for signal processors using sine-wave and noise-band outputs. J Acoust Soc Am, 1997. 102(4): p. 2403-11.

Shannon, R.V., F.G. Zeng, and J. Wygonski, Speech recognition with altered spectral distribution of envelope cues. J Acoust Soc Am, 1998. 104(4): p. 2467-76.

Fu, Q.J. and R.V. Shannon, Recognition of spectrally degraded and frequency-shifted vowels in acoustic and electric hearing. J Acoust Soc Am, 1999. 105(3): p. 1889-900.

Green, T., A. Faulkner, and S. Rosen, Spectral and temporal cues to pitch in noise-excited vocoder simulations of continuous-interleaved-sampling cochlear implants. J Acoust Soc Am, 2002. 112(5 Pt 1): p. 2155-64.

Moore, BCJ, Coding of sounds in the auditory system and its relevance to signal processing and coding in cochlear implants. Otology & neurotology, 2003.

Loizou, PC, Speech processing in vocoder-centric cochlear implants, Advances in Oto Rhino Laryngology, 2006.

Johnson, D.H., The relationship between spike rate and synchrony in responses of auditory-nerve fibers to single tones. J Acoust Soc Am, 1980. 68(4): p. 1115-22.

Joris, P.X. and T.C. Yin, Responses to amplitude-modulated tones in the auditory nerve of the cat. J Acoust Soc Am, 1992. 91(1): p. 215-32.

Tasaki, I., Nerve impulses in individual auditory nerve fibers of guinea pig. J Neurophysiol, 1954. 17(2): p. 97-122.

Rose, J.E., et al., Phase-locked response to low-frequency tones in single auditory nerve fibers of the squirrel monkey. J Neurophysiol, 1967. 30(4): p. 769-93.

Rupert, A., G. Moushegian, and R. Galambos, Unit responses to sound from auditory nerve of the cat. J Neurophysiol, 1963. 26: p. 449-65.

Oxenham, A.J., Revisiting place and temporal theories of pitch. Acoust Sci Technol, 2013. 34(6): p. 388-396.

Drullman, R., Temporal envelope and fine structure cues for speech intelligibility. J Acoust Soc Am, 1995. 97(1): p. 585-92.

Shannon, R.V., et al., Speech recognition with primarily temporal cues. Science, 1995. 270(5234): p. 303-4.

Moon, I.J. and S.H. Hong, What is temporal fine structure and why is it important? Korean J Audiol, 2014. 18(1): p. 1-7.

Shamma, S. and C. Lorenzi, On the balance of envelope and temporal fine structure in the encoding of speech in the early auditory system. J Acoust Soc Am, 2013. 133(5): p. 2818-33.

Wilson, B.S., Getting a decent (but sparse) signal to the brain for users of cochlear implants. Hear Res, 2015. 322: p. 24-38.

Hill, F.J., L.P. McRae, and R.P. McClellan, Speech recognition as a function of channel capacity in a discrete set of channels. J Acoust Soc Am, 1968. 44(1): p. 13-8.

Shannon, R.V., et al., Speech perception with cochlear implants., in Cochlear implants: Auditory protheses and electric hearing., F.-G. Zheng, A.N. Popper, and R.R. Fay, Editors. 2006, Springer New York. p. 334-376.

Gnansia, D., et al., Effects of spectral smearing and temporal tine structure degradation on speech masking release. J Acoust Soc Am, 2009. 125(6): p. 4023-33.

(56) References Cited

OTHER PUBLICATIONS

Hopkins, K. and B.C. Moore, The contribution of temporal fine structure to the intelligibility of speech in steady and modulated noise. J Acoust Soc Am, 2009. 125(1): p. 442-6.
Swaminathan, J. and M.G. Heinz, Psychophysiological analyses demonstrate the importance of neural envelope coding for speech perception in noise. J Neurosci, 2012. 32(5): p. 1747-56.
Qin, M.K. and A.J. Oxenham, Effects of simulated cochlear-implant processing on speech reception in fluctuating maskers. J Acoust Soc Am, 2003. 114(1): p. 446-54.
Nile, K., G. Stickney, and F.G. Zeng, Encoding frequency modulation to improve cochlear implant performance in noise. IEEE Trans Biomed Eng, 2005. 52(1): p. 64-73.
Dillier, N., et al., Encoding and decoding of auditory signals in relation to human speech and its application to human cochlear implants. Audiology, 1980. 19(2): p. 146-63.
Wilson, B.S., et al., Better speech recognition with cochlear implants. Nature, 1991. 352(6332): p. 236-8.
Koch, D.B., et al., Using current steering to increase spectral resolution in CII and HiRes 90K users. Ear Hear, 2007. 28(2 Suppl): p. 38S-41S.
Firszt, J.B., et al., Current steering creates additional pitch percepts in adult cochlear implant recipients. Otol Neurotol, 2007. 28(5): p. 629-36.
Spahr, A.J., et al., Simulating the effects of spread of electric excitation on musical tuning and melody identification with a cochlear implant. J Speech Lang Hear Res, 2008. 51(6): p. 1599-606.
Bonham, B.H. and L.M Litvak, Current focusing and steering: modeling, physiology, and psychophysics. Hear Res, 2008. 242(1-2): p. 141-53.
Hu, Y. and P.C. Loizou, A new sound coding strategy for suppressing noise in cochlear implants. J Acoust Soc Am, 2008. 124(1): p. 498-509.
Buechner, A., et al., A high rate n-of-m speech processing strategy for the first generation Clarion cochlear implant. Int J Audiol, 2009. 48(12): p. 868-75.
Tyler, R.S., et al., Evaluation of different choices of n in an n of m processor for cochlear implants. Adv Otorhinolaryngol, 2000. 57: p. 311-5.
Stickney, G.S., K. Nie, and F.G. Zeng, Contribution of frequency modulation to speech recognition in noise. J Acoust Soc Am, 2005. 118(4): p. 2412-20.
Zeng, F.G., et al., Speech recognition with amplitude and frequency modulations. Proc Natl Acad Sci U S A, 2005. 102(7): p. 2293-8.
Wilson, B.S., et al., Coding strategies for multichannel cochlear prostheses. Am J Otol, 1991. 12 Suppl: p. 56-61.
Faltys, M.A., et al., Multichannel cochlear prosthesis with flexible control of stimulus waveforms. 2001, Google Patents.
Melo, T.M., M.C. Bevilacqua, and O.A. Costa, Speech perception in cochlear implant users with the HiRes 120 strategy: a systematic review. Braz J Otorhinolaryngol, 2012. 78(3): p. 129-33.
Chang, Y.T., et al., Tone discrimination and speech perception benefit in Mandarin-speaking children fit with HiRes fidelity 120 sound processing. Otol Neurotol, 2009. 30(6): p. 750-7.
Firszt, J.B., et al., Speech recognition in cochlear implant recipients: comparison of standard HiRes and HiRes 120 sound processing. Otol Neurotol, 2009. 30(2): p. 146-52.
Han, D., et al., Lexical tone perception with HiResolution and HiResolution 120 sound-processing strategies in pediatric Mandarin-speaking cochlear implant users. Ear Hear, 2009. 30(2): p. 169-77.
Kos, M.I., et al., Immuno-detection of *Staphylococcus aureus* biofilm on a cochlear implant. Infection, 2009. 37(5): p. 450-4.
Landsberger, D.M. and A.G. Srinivasan, Virtual channel discrimination is improved by current focusing in cochlear implant recipients. Hear Res, 2009. 254(1-2): p. 34-41.
Park, H.J., et al., HiRes with Fidelity 120 benefit in native speakers of Korean. Cochlear Implants Int, 2009. 10 Suppl 1: p. 85-8.

Runge-Samuelson, C.L., Effects of high-rate pulse trains on electrode discrimination in cochlear implant users. Trends Amplif, 2009. 13(2): p. 76-86.
Donaldson, G.S., P.K. Dawson, and L.Z. Borden, Within-subjects comparison of the HiRes and Fidelity120 speech processing strategies: speech perception and its relation to place-pitch sensitivity. Ear Hear, 2011. 32(2): p. 238-50.
Kam, A.C., et al., Evaluation of the ClearVoice Strategy in Adults Using HiResolution Fidelity 120 Sound Processing. Clin Exp Otorhinolaryngol, 2012. 5 Suppl 1: p. S89-92.
Greenwood, D.D., A cochlear frequency-position function for several species—29 years later. The Journal of the Acoustical Society of America, 1990. 87(6): p. 2592-2605.
Nogueira, W., et al., Design and evaluation of a cochlear implant strategy based on a "Phantom" channel. PLoS One, 2015. 10(3): p. e0120148.
Fridman, G.Y., Methods and apparatus for cochlear implant signal processing. 2011, Google Patents.
Voelkel, A.W., Stimulation channel selection methods. 2010, Google Patents.
Nobbe, A., et al., Frequency discrimination with sequential or simultaneous stimulation in MED-EL cochlear implants. Acta otolaryngologica, 2007. 127(12): p. 1266-1272.
Zierhofer, C.M., Electrical nerve stimulation based on channel specific sampling sequences. 2003, Google Patents.
Neal, T. and B. van Dijk, Determining stimulation signals for neural stimulation. 2015, Google Patents.
James, C.J, Stimulation channel selection for a stimulating medical device. 2012, Google Patents.
Vandali, A. and G.M. Clark, Emphasis of short-duration transient speech features 2008, Google Patents.
Korean Intellectual Property Office (ISA/KE), "International Search Report for PCT/US2016/041768", Korea, Oct. 21, 2016.
Shepherd, R.K. and N.A. Hardie, Deafness-induced changes in the auditory pathway: implications for cochlear implants. Audiology & neuro-otology, 2001. 6(6): p. 305-18.
Zeng F.G., Q. Tang, and T. Lu, Abnormal pitch perception produced by cochlear implant stimulation. PloS one, 2014. 9(2): p. e88662.
Shepherd, R.K. and E. Javel, Electrical stimulation of the auditory nerve. I. Correlation of physiological responses with cochlear status. Hearing research, 1997. 108(1-2): p. 112-44.
Hartmann, R., G. Topp, and R. Klinke, Discharge patterns of cat primary auditory fibers with electrical stimulation of the cochlea. Hearing research, 1984. 13(1): p. 47-62.
van den Honert, C. and P.H. Stypulkowski, Single fiber mapping of spatial excitation patterns in the electrically stimulated auditory nerve. Hearing research, 1987. 29(2-3): p. 195-206.
van den Honert, C. and P.H. Stypulkowski, Physiological properties of the electrically stimulated auditory nerve. II. Single fiber recordings. Hearing research, 1984. 14(3): p. 225-43.
Tirko, N.N. and D.K. Ryugo, Synaptic plasticity in the medial superior olive of hearing, deaf, and cochlear-implanted cats. The Journal of comparative neurology, 2012. 520(10): p. 2202-17.
Baker, C.A., et al., Postnatal development of the endbulb of held in congenitally deaf cats. Frontiers in neuroanatomy, 2010. 4: p. 19.
Ryugo, D.K., et al., Separate forms of pathology in the cochlea of congenitally deaf white cats. Hearing research, 2003. 181(1-2): p. 73-84.
Redd, E.E., et al., The effects of congenital deafness on auditory nerve synapses: Type I and Type II multipolar cells in the anteroventral cochlear nucleus of cats. Journal of the Association for Research in Otolaryngology: JARO, 2002. 3(4): p. 403-17.
Redd, E.E., T. Pongstaporn, and D.K. Ryugo, The effects of congenital deafness on auditory nerve synapses and globular bushy cells in cats. Hearing research, 2000. 147(1-2): p. 160-74.
Ryugo, D.K., et al., Ultrastructural analysis of primary endings in deaf white cats: morphologic alterations in endbulbs of Held. The Journal of comparative neurology, 1997. 385(2): p. 230-44.
Saada, A.A., J.K. Niparko, and D.K. Ryugo, Morphological changes in the cochlear nucleus of congenitally deaf white cats. Brain research, 1996. 736(1-2): p. 315-28.

(56) References Cited

OTHER PUBLICATIONS

Limb, C.J., et al., Auditory cortical activity during cochlear implant-mediated perception of spoken language, melody, and rhythm. Journal of the Association for Research in Otolaryngology : JARO, 2010. 11(1): p. 133-43.

Naito, Y., et al., Increased cortical activation during hearing of speech in cochlear implant users. Hearing research, 2000. 143(1-2): p. 139-46.

Wong, D., et al., PET imaging of cochlear-implant and normal-hearing subjects listening to speech and nonspeech. Hearing research, 1999. 132(1-2): p. 34-42.

Gfeller, K., et al., The effects of familiarity and complexity on appraisal of complex songs by cochlear implant recipients and normal hearing adults. Journal of music therapy, 2003. 40(2): p. 78-112.

Stordahl, J., Song recognition and appraisal: a comparison of children who use cochlear implants and normally hearing children. Journal of music therapy, 2002. 39(1): p. 2-19.

Aggarwal, R. and K.M. Green, Cochlear implants and positron emission tomography. The Journal of laryngology and otology, 2012. 126(12): p. 1200-3.

Green, K.M., et al., Cortical plasticity in the first year after cochlear implantation. Cochlear implants international, 2008. 9(2): p. 103-17.

Coez, A., et al., Cochlear implant benefits in deafness rehabilitation: PET study of temporal voice activations. Journal of nuclear medicine : official publication, Society of Nuclear Medicine, 2008. 49(1): p. 60-7.

Naito, Y., et al., Development and plasticity of the auditory cortex in cochlear implant users: a follow-up study by positron emission tomography. Advances in oto-rhino-laryngology, 2000. 57: p. 55-9.

Miyamoto, R.T. and D. Wong, Positron emission tomography in cochlear implant and auditory brainstem implant recipients. Journal of communication disorders, 2001. 34(6): p. 473-8.

Hirano, S., et al., Functional differentiation of the auditory association area in prelingually deaf subjects. Auris, nasus, larynx, 2000. 27(4): p. 303-10.

Truy, E., et al., Auditory cortex activity changes in long-term sensorineural deprivation during crude cochlear electrical stimulation: evaluation by positron emission tomography. Hearing research, 1995. 86(1-2): p. 34-42.

Shannon, R.V., Q.J. Fu, and J. Galvin, 3rd, The number of spectral channels required for speech recognition depends on the difficulty of the listening situation. Acta oto-laryngologica. Supplementum, 2004(552): p. 50-4.

Fishman, K.E., R.V. Shannon, and W.H. Slattery, Speech recognition as a function of the number of electrodes used in the SPEAK cochlear implant speech processor. Journal of speech, language, and hearing research : JSLHR, 1997. 40(5): p. 1201-15.

Reiss, L.A., et al., Consonant recognition as a function of the number of stimulation channels in the Hybrid short-electrode cochlear implant. The Journal of the Acoustical Society of America, 2012. 132(5): p. 3406-17.

Snel-Bongers, J., et al., Spread of excitation and channel interaction in single- and dual-electrode cochlear implant stimulation. Ear and hearing, 2012. 33(3): p. 367-76.

Dorman, M., et al., Consonant recognition as a function of the number of channels of stimulation by patients who use the Symbion cochlear implant. Ear and hearing, 1989. 10(5): p. 288-91.

Shannon, R.V., Multichannel electrical stimulation of the auditory nerve in man. II. Channel interaction. Hearing research, 1983. 12(1): p. 1-16.

Shannon, R.V., Multichannel electrical stimulation of the auditory nerve in man. I. Basic psychophysics. Hearing research, 1983. 11(2): p. 157-89.

Kral, A., et al., Spatial resolution of cochlear implants: the electrical field and excitation of auditory afferents. Hearing research, 1998. 121(1-2): p. 11-28.

Liang, D.H., H.S. Lusted, and R.L. White, The nerve-electrode interface of the cochlear implant: current spread. IEEE transactions on bio-medical engineering, 1999. 46(1): p. 35-43.

Black, R.C., et al., Current distributions in cochlear stimulation. Annals of the New York Academy of Sciences, 1983. 405: p. 137-45.

Micco, A.G. and C.P. Richter, Tissue resistivities determine the current flow in the cochlea. Current opinion in otolaryngology & head and neck surgery, 2006. 14(5): p. 352-5.

Micco, A.G. and C.P. Richter, Electrical resistivity measurements in the mammalian cochlea after neural degeneration. The Laryngoscope, 2006. 116(8): p. 1334-41.

Firszt, J.B., et al., Current steering creates additional pitch percepts in adult cochlear implant recipients. Otology & neurotology : official publication of the American Otological Society, American Neurotology Society [and] European Academy of Otology and Neurotology, 2007. 28(5): p. 629-36.

Baskent, D. and R.V. Shannon, Interactions between cochlear implant electrode insertion depth and frequency-place mapping. The Journal of the Acoustical Society of America, 2005. 117(3 Pt 1): p. 1405-16.

Nelson, D.A., et al., Intensity discrimination as a function of stimulus level with electric stimulation. The Journal of the Acoustical Society of America, 1996. 100(4 Pt 1): p. 2393-414.

Smith, Z.M., B. Delgutte, and A.J. Oxenham, Chimaeric sounds reveal dichotomies in auditory perception. Nature, 2002. 416(6876): p. 87-90.

Voelcker, H.B., Toward a unified theory of modulation. Proceedings of the IEEE, 1966. 54(3): p. 340.

Rice, S.O., Distortion produced by band limitation of an FM wave. The Bell System Technical Journal, 1973. 52(5): p. 605-626.

Logan, B.F.J., Information in the zero crossings of bandpass signals. The Bell System Technical Journal, 1977. 56(4): p. 487-510.

Sachs, M.B., Neural coding of complex sounds: speech. Annu Rev Physiol, 1984. 46: p. 261-73.

Whiteford, K.L. and A.J. Oxenham, Using individual differences to test the role of temporal and place cues in coding frequency modulation. J Acoust Soc Am, 2015. 138(5): p. 3093.

Javel, E. and J.B. Mott, Physiological and psychophysical correlates of temporal processes in hearing. Hear Res, 1988. 34(3): p. 275-94.

Rutherford, W., A New Theory of Hearing. J Anat Physiol, 1886. 21(Pt 1): p. 166-8.

Wever, E.G. and C.W. Bray, Action Currents in the Auditory Nerve in Response to Acoustical Stimulation. Proc Natl Acad Sci U S A, 1930. 16(5): p. 344-50.

Wever, E.G. and C.W. Bray, Auditory Nerve Impulses. Science, 1930. 71(1834): p. 215.

\* cited by examiner

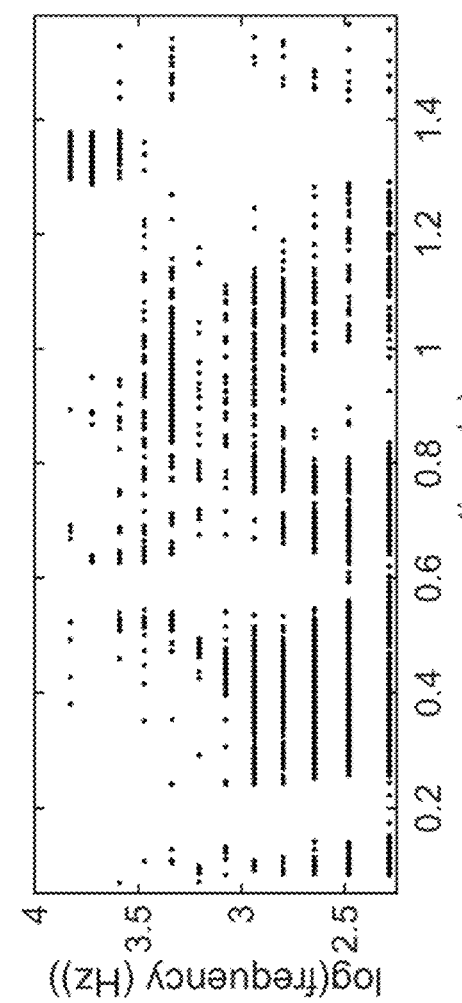
FIG. 7A
FIG. 7B

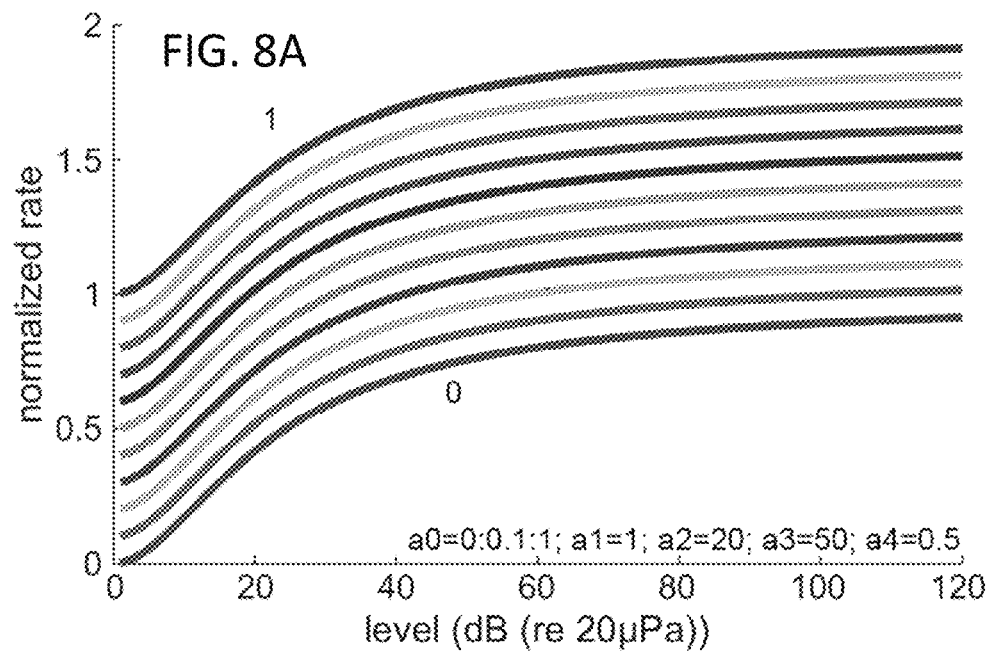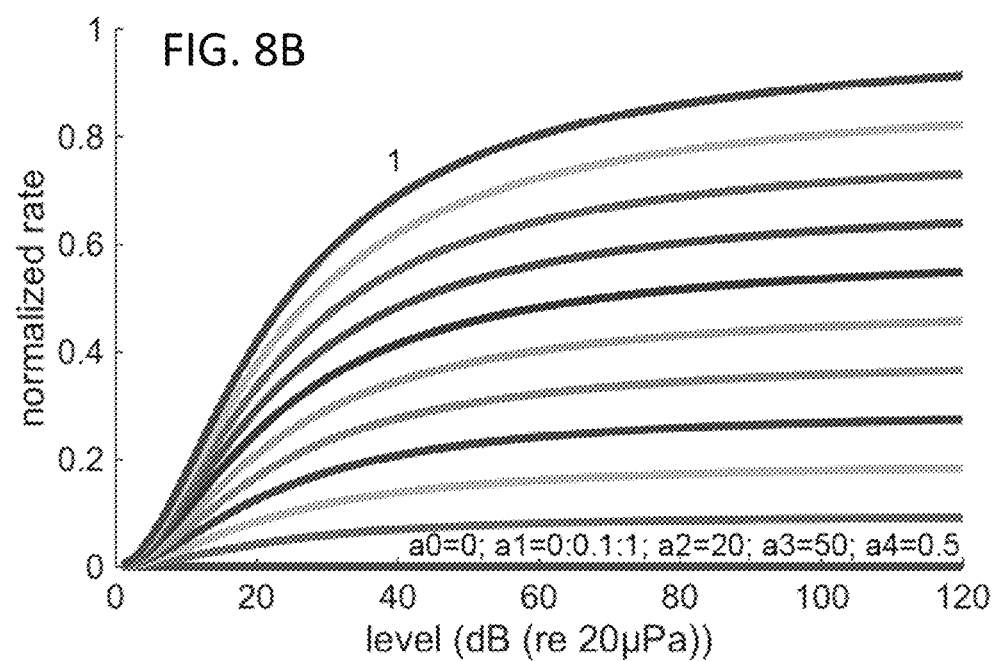

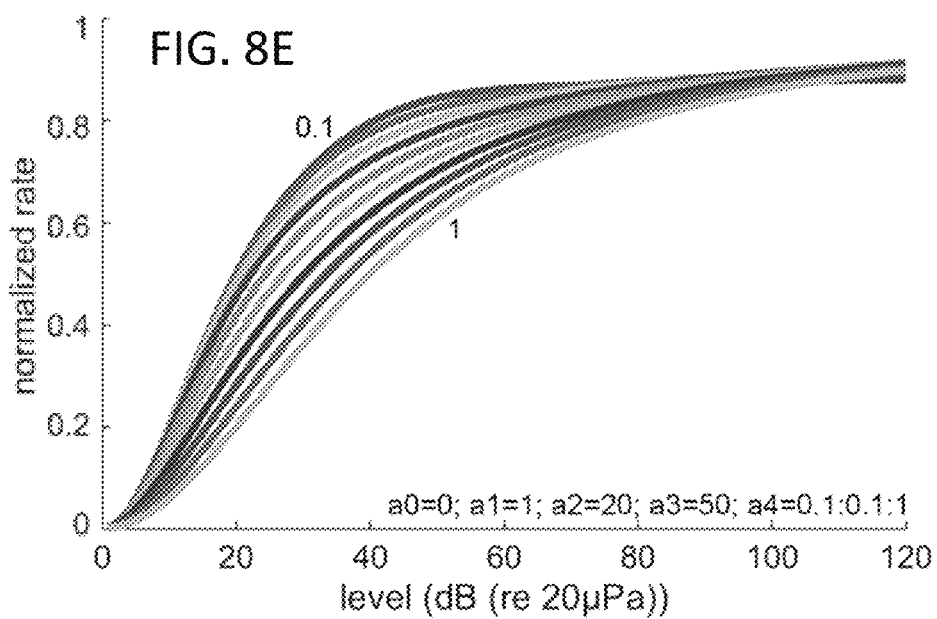

| | | age | gender | implanted left | implanted right | left | right | other |
|---|---|---|---|---|---|---|---|---|
| participants | | | | | | | | |
| Med-El | | | | | | | | |
| #4573 | S1 | 34 | male | 01-2012 | 01-2014 | Rondo on Concerto | Med-El-Opus II on Sonata | |
| R0058 | S2 | 54 | male | 06-2015 | none | Rondo on Synchrony | hearing aid | |
| R0133 | S3 | | male | | none | | | |
| R0940 | S4 | 75 | female | none | 11-2012 | none | Opus II on Concerto | |
| #1270 | S5 | 82 | female | 03-2013 | 01-2011 | Rondo on Concerto | Rondo on Sonata | |
| #1082 | S6 | 99 | female | none | 06-2015 | none | Sonnet on Concerto | tinnitus |
| R2288 | S7 | 88 | female | 06-2012 | none | Opus II on Concerto | hearing aid | |
| #7884 | S8 | 90 | male | 06-2015 | none | Sonnet on Synchrony | none | |
| R6147 | S9 | 70 | female | none | 10-2012 | none | Opus II on Concerto | tinnitus |
| R6549 | S10 | 69 | female | none | 01-2015 | none | Opus II on Concerto | |
| R6924 | S11 | | | | | | | |
| Advanced Bionics | | | | | | | | |
| F1018 | S11 | | male | none | 01-2015 | hearing aid | AB | |
| R8215 | S12 | | | ~2010 | none | AB | hearing aid | tinnitus |
| F1176 | S13 | | | | | | | |
| F7023 | S14 | | | | | | | |
| R0924 | S15 | | | 2002 | 2007 | AB | AB | |
| #6920 | S16 | | | | | | | |

FIG. 10

| Med-El | | | | |
|---|---|---|---|---|
| | before training | after training | MedEl | years of use |
| | % correct | | | |
| #4573_1 | 0 | 60 | 94 | 3+/1.5 |
| #9058_1 | 0 | 80 | | <0.5 |
| #9133_1 | 0 | 42 | 85 | 6+ |
| #0940_1 | 0 | 49 | 98 | 2.5 |
| #1270_1 | 0 | 57 | 70 | 2.0 |
| #4062_1 | 0 | 0 | 58 | 0.3 |
| #2288_1 | 0 | 0 | 0 | 0.3 |
| #7884_1 | 0 | 87 | 77 | 0.3 |
| #1270_2 | 0 | 51 | | 2.0 |
| #1270_2 | 6 | 56 | | 2.0 |
| #9058_3 | | | 98 | <0.5 |
| #4573_2 | 21 | 66 | 96 | 3+/1.5 |
| #8147_1 | 0 | 83 | 100 | 2.0 |
| #6549_1 | 0 | 17 | 42 | 1.0 |
| AB | | | | |
| | before training | after training | AB | years of use |
| | % correct | | | |
| #1018_1 | 0 | 10 | 40 | |
| #1175_1 | 9.8 | 100 | TBD | |
| #7023_1 | 0 | 71 | TBD | |
| #8215_1 | 0 | 17.3 | 79.2 | 6 |
| #6924_1 | 0 | 96.1 | TBD | |
| #6820_1 | 19.6 | 82 | TBD | |

FIG. 11

| | #4573_1 | #4573_2 | #4573_2 | #9058_1 | #9058_1 | #1270_1 | #1270_1 | #4062_1 | #2289_1 | #2289_1 |
|---|---|---|---|---|---|---|---|---|---|---|
| | 20150718 | 20150730 | 20150724 | 20150916 | 20150916 | 20150923 | 20150923 | 20150930 | 20151007 | 20151007 |
| | HINT 1 | HINT 1 | HINT 2 | HINT 1 | HINT 2 | HINT 1 | HINT 2 | HINT 1 | HINT 1 | HINT 2 |
| | 0 | 45 | 15 | 0 | 8 | 0 | 11 | 0 | 0 | |
| | 0 | | training | 0 | training | 0 | training | 0 | 0 | |
| FMPC | training | | 27 | 0 | 50.3 | training | training | training | 0 | |
| | training | | 25 | training | 50.3 | training | training | training | training | |
| | training | | 38.5 | training | | training | 53 | 0 | training | |
| | 41.5 | | | 32.3 | | 56.6 | | | voume ← | |
| | 60.4 | | | 44 | | | | | 0 | |
| | 60.4 | | | 80 | | | | | training | |
| MedEl | 94.3 | | | | | 67.5 | 70.3 | 49 | 0 | 86.5 |
| Hearing aid | | | | | | | | | 94.3 | |
| MedEl+ HA | | | | | | | | | 77.4 | 96.2 |
| FMPC+HA | | | | | | | | | 88.7 | 88.4 |
| timber test CPRC | | | | | | | | | | |
| timber test MedEl | | | | | | | | | | |

FIG. 14A

| #7884_1 | #9058_2 | #1270_2 | #1270_2 | #9058_3 | #9058_3 | #9058_4 | #9058_4 | #8147_1 | #8147_1 |
|---|---|---|---|---|---|---|---|---|---|
| 20151014 | 20151014 | 20151020 | 20151020 | 20151022 | 20151022 | 20151105 | 20151105 | 20151209 | 20151209 |
| H1N1 | H1N1 | H1N1 | H1N2 | H1N1 | H1N2 | H1N3 | H1N1 | H1N2 | H1N1 | H1N2 |
| 0 | 0 | 0 | 5.8 | | 17 | 32 | 17 | 38 | 11 | 0 |
| training | training | training | training | | 40 | | training | training | 11 | training |
| volume ← | | training | 55.8 | | | | 66 | 65 | 11 | 67 |
| volume ← | | 50.9 | | | | | | | training | |
| 1.9 | | | | | | | | | training | |
| training | | | | | | | | | training | |
| 78.3 | | | | | | | | | 83 | |
| 67.9* | | | | | | | | | 70 | |
| 20.8* | | | | | | | | | | |
| 86.8* | | | | | | | | | | |
| | | | | | | | | | | |
| | | | | 98 | 100 | | | | 98 | 100 |
| 77.4* | | | | | | | | | | |

FIG. 14B

| #9058_4 | #0940_1 | #6549_1 | #9058_5 | #9133_1 | #1175 | #7023 | #8215 | #1018 | #6924 |
|---|---|---|---|---|---|---|---|---|---|
| 20151612 | 20160106 | 20160114 | 20160118 | | 20150519 | 20160520 | 20160602 | 20160606 | 20160611 |
| HINT2 | HINT1 | HINT1 | HINT2 | | HINT6 | HINT6 | HINT8 | HINT6 | HINT6 |
| 23 | 0 | 0 | 25 | | 0 | 0 | 0 | 0 | 0 |
| training | training | training | training | | 9.8 | training | training | training | training |
| 67 | 0 | 0 | 54 | | 7.8 | training | training | training | training |
| | training | training | opti | | training | 70.6 | 17.3 | 9.8 | 96.1 |
| | 11 | 17 | 21 | 32 | training | HINT7 | HINT9 | HINT7 | HINT7 |
| | 8 | 42 | training | 42 | 100 | 16.9% | 6% | 0 | 66 |
| | 13 | 42 | 62 | | HINT7 | training | training | training | training |
| | 47 | | | | 30.2 | 56.6 | | | training |
| | 49 | | | | training | | 16 | 11.8 | 90.6 |
| | | | | | 77.4 | | | | |
| | | | | | HINT6 | | | | |
| | | | | | 72.5 | | | | |
| | | | | | | | | | |
| | | | | 85 | | | | | |
| 98 | 98 | 42 | | | | | | 9.6 (40.4) | |
| 16.6 | | | | | | | | | |
| 25 | | | | | | | | | |

FIG. 14C

|  | classical | | | | R&B | | | | rock | | |
|---|---|---|---|---|---|---|---|---|---|---|---|
|  | FMPC | Med-EI | factor | | FMPC | Med-EI | factor | | FMPC | Med-EI | factor |
|  | power [J/s] | power [J/s] | | | power [J/s] | power [J/s] | | | power [J/s] | power [J/s] | |
| e1 | 9.02E-08 | 3.97E-08 | 0.43 | e1 | 9.30E-08 | 8.39E-08 | 0.9 | e1 | 6.66E-08 | 4.80E-08 | 0.72 |
| e2 | 1.82E-07 | 2.28E-07 | 1.25 | e2 | 1.43E-07 | 4.09E-07 | 2.86 | e2 | 1.00E-07 | 3.84E-07 | 3.84 |
| e3 | 3.34E-07 | 1.26E-06 | 3.76 | e3 | 2.66E-07 | 2.02E-06 | 7.53 | e3 | 1.80E-07 | 1.47E-06 | 8.16 |
| e4 | 4.41E-07 | 2.98E-06 | 6.75 | e4 | 2.48E-07 | 2.93E-06 | 11.81 | e4 | 1.44E-07 | 2.40E-06 | 16.62 |
| e5 | 5.43E-07 | 1.53E-06 | 2.82 | e5 | 3.20E-07 | 1.15E-06 | 3.58 | e5 | 1.53E-07 | 1.36E-06 | 8.64 |
| e6 | 7.54E-07 | 5.59E-07 | 0.74 | e6 | 1.13E-07 | 8.74E-07 | 7.74 | e6 | 3.29E-07 | 1.76E-06 | 5.35 |
| e7 | 3.36E-07 | 5.45E-07 | 1.63 | e7 | 4.79E-08 | 7.14E-07 | 14.9 | e7 | 1.63E-07 | 1.58E-06 | 9.67 |
| e8 | 3.75E-07 | 9.25E-07 | 2.47 | e8 | 9.56E-08 | 1.37E-06 | 14.31 | e8 | 1.34E-07 | 2.10E-06 | 15.63 |
| e9 | 3.00E-07 | 2.95E-07 | 0.98 | e9 | 9.24E-08 | 7.30E-07 | 7.9 | e9 | 1.56E-07 | 1.33E-06 | 8.54 |
| e10 | 3.64E-07 | 2.41E-07 | 0.66 | e10 | 1.89E-07 | 5.89E-07 | 3.11 | e10 | 9.21E-08 | 8.22E-07 | 8.93 |
| average | 3.72E-07 | 8.60E-07 | 2.15 | average | 1.61E-07 | 1.09E-06 | 7.46 | average | 1.52E-07 | 1.32E-06 | 8.61 |

|  | rate [Hz] | | | | rate [Hz] | | | | rate [Hz] | | |
|---|---|---|---|---|---|---|---|---|---|---|---|
| e1 | 817 | 4022 | 0.2 | e1 | 828 | 1986 | 0.42 | e1 | 898 | 1424 | 0.49 |
| e2 | 1188 | 1752 | 0.68 | e2 | 1052 | 1938 | 0.54 | e2 | 880 | 2093 | 0.42 |
| e3 | 1386 | 3707 | 0.37 | e3 | 1240 | 3714 | 0.33 | e3 | 1014 | 3708 | 0.27 |
| e4 | 1620 | 3708 | 0.44 | e4 | 1212 | 3712 | 0.33 | e4 | 924 | 3714 | 0.25 |
| e5 | 1924 | 3716 | 0.52 | e5 | 1472 | 3706 | 0.4 | e5 | 1034 | 3710 | 0.28 |
| e6 | 2196 | 3666 | 0.6 | e6 | 848 | 3667 | 0.23 | e6 | 1448 | 3718 | 0.39 |
| e7 | 1546 | 3648 | 0.42 | e7 | 584 | 3629 | 0.16 | e7 | 1078 | 3710 | 0.29 |
| e8 | 1568 | 3684 | 0.43 | e8 | 790 | 3694 | 0.21 | e8 | 936 | 3714 | 0.25 |
| e9 | 1465 | 3547 | 0.41 | e9 | 812 | 3656 | 0.22 | e9 | 1054 | 3714 | 0.28 |
| e10 | 1485 | 3508 | 0.42 | e10 | 1070 | 3651 | 0.29 | e10 | 746 | 3678 | 0.2 |
| average | 1519.70 | 3495.80 | 0.45 | average | 990.8 | 3335.30 | 0.31 | average | 1001.2 | 3318.30 | 0.31 |

FIG. 20

| | FMPC | | | | | | Med-El | | | | | |
|---|---|---|---|---|---|---|---|---|---|---|---|---|
| | #9058 | #8147 | #9133 | #4573 | #6549 | #0940 | #9058 | #8147 | #9133 | #4573 | #6549 | #0940 |
| speech | | | | | | | | | | | | |
| changes with level | y | y | y | y | y | y | n | | y | y | y | y |
| gender identification | y | y | y | y | y | y | y | y | y | y | y | y |
| rhythm or speed pattern | y | y | y | y | y | y | y | y | y | y | y | y |
| sentence structure | y | y | y | y | y | y | y | y | y | y | y | y |
| can imagine words | n | y | y | y | y | y | n | y | y | y | y | y |
| loudness variation | y | n | y | y | y | y | y | y | y | y | y | y |
| word recognition | | | y | y | y | y | | | | | | |
| improves with training | n | y | n | n | n | | n | n | n | n | n | n |
| memorize sentences/words | y | y | n | y | y | | y | y | y | y | y | n |
| music | | | | | | | | | | | | |
| recognizes beats | y | y | y | y | y | n | y | y | y | y | y | y |
| recognizes music | y | n | y | y | y | n | n | y | y | y | y | y |
| recognizes song titles | n | y | n | n | n | n | y | y | y | y | y | y |
| recognizes vocals | y | y | y | y | y | n | y | y | y | y | y | y |
| recognizes different instruments | n | n | n | n | n | n | n | n | y | y | y | y |
| understands lyrics | n | n | y | n | n | n | n | y | n | y | y | y |
| recognizes string instruments | n | n | n | n | n | n | y | y | y | n | y | y |
| recognizes wind instruments | n | n | n | n | n | n | y | n | y | n | y | y |
| recognizes guitar | n | n | n | n | n | n | n | n | y | n | n | n |
| recognizes drums | y | y | n | n | n | n | y | n | n | n | n | n |
| recognizes violin | n | n | n | n | n | n | n | n | n | n | n | n |
| can distinguish notes | n | y | n | n | n | n | n | n | y | y | y | n |

FIG. 21

| Participant | FMPC | | Med-El | |
|---|---|---|---|---|
| | % correct | | % correct | |
| #9133 (Med-El) | 4 | | 58 | |
| #9058 (Med-El) | 16.6 | | 25 | |
| #6924 (AB) | 33 | | 62.5 | |
| | | | | |

FIG. 22

METHODS OF FREQUENCY-MODULATED PHASE CODING (FMPC) FOR COCHLEAR IMPLANTS AND COCHLEAR IMPLANTS APPLYING SAME

CROSS-REFERENCE TO RELATED PATENT APPLICATIONS

This application claims priority to and the benefit of, pursuant to 35 U.S.C. §119(e), U.S. Provisional Patent Application Ser. No. 62/191,084, filed Jul. 10, 2015, entitled "SYSTEMS AND METHODS FOR NOISE BASED CODING IN COCHLEAR IMPLANTS", by Claus-Peter Richter et al., and U.S. Provisional Patent Application Ser. No. 62/320,132, filed Apr. 8, 2016, entitled "SYSTEMS AND METHODS FOR FREQUENCY MODULATED PHASE CODING (FMPC) FOR COCHLEAR IMPLANTS", by Claus-Peter Richter et al. Each of the above-identified applications is incorporated herein by reference in its entirety.

Some references, which may include patents, patent applications, and various publications, are cited in a reference list and discussed in the description of this invention. The citation and/or discussion of such references is provided merely to clarify the description of the invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [36] represents the 36th reference cited in the reference list, namely, Micco, A. G. and C. P. Richter, *Tissue resistivities determine the current flow in the cochlea.* Current opinion in otolaryngology & head and neck surgery, 2006. 14(5): p. 352-5.

STATEMENT AS TO RIGHTS UNDER FEDERALLY-SPONSORED RESEARCH

This invention was made with government support under R01 DC011855 awarded by the National Institutes of Health. The government has certain rights in the invention.

FIELD OF THE INVENTION

The invention relates generally to neural stimulation, and more particularly to a method of frequency-modulated phase coding (FMPC) for cochlear implants and cochlear implants applying the same.

BACKGROUND OF THE INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

Cochlear implants are neural prostheses that help severely-to-profoundly deaf people to restore some hearing. Physically, three components can be identified, the speech processor with its transmission coil, the receiver and stimulator, and the cochlear implant electrode array. The speech processor receives sound from one or more microphones and converts the sound into a corresponding electrical signal. While the hearing range of a young healthy human is typically between 0.02 and 20 kHz, it has been assumed for coding of acoustic information in cochlear implants that most of the information used for communication is in the frequency range between 0.1 and 8 kHz. The frequency band from 0.1 to 8 kHz is divided into many smaller frequency bands of about 0.5 octaves width. The number of small frequency bands is determined by the number of electrodes along the electrode array, which is inserted into the cochlea. Each frequency band is then treated by a mathematical algorithm, such as a Hilbert transform that extracts the envelope of the filtered waveform. The envelope is then transmitted via an ultrahigh frequency (UHF) connection across the skin to a receiver coil, which was surgically implanted behind the ear. The envelope is used to modulate a train of pulses with a fixed pulse repetition rate. For each of the electrodes, a train of pulses with fixed frequency and fixed phase is used to stimulate the cochlear nerve. Multiple algorithms have been implemented to select a group of 4-8 electrode contacts for simultaneous stimulation.

Biological Constraints that Affect Performance of Cochlear Implants:

Damage of cochlear neural structures can result in severe deafness. Depending on the neural degeneration in the cochlea performance, the performance of a cochlear implant user may vary. Changes that occur include the demyelination and degeneration of dendrites and neuronal death [1]. The neuronal loss can be non-uniform and results in "holes" of neurons along the cochlea. Holes lead to distortion of the frequency maps, which affects speech recognition [2]. Caused by changes in myelination and synapse size, changes in firing properties of the nerve were described such as prolonged delay times and changed refractory periods [3-6]. In the brainstem and midbrain the neuronal connections appear to remain intact. However, a decrease in neuron size, afferent input, synapse size and density can be detected [7-13]. Neural recordings reveal a change in response properties that adversely affect temporal resolution such as elevated thresholds, de-synchronization, increased levels of neural adaptation, increased response latencies. A loss of inhibitory influences has been described. At the cortex, spatially larger cortical activation was seen with (PET) [1, 14-16]. The findings support a plastic reorganization and more intense use of present auditory networks [15, 17-25].

Technical Constraints that Affect Performance of Cochlear Implants:

A normal functioning cochlea has 3000-3500 hair cells to encode the acoustic information along the cochlea. More than 30 perceptual channels can be processed in parallel [26]. The entire frequency range is between 0.02 and 20 kHz where high frequencies are encoded in the cochlear base and low frequencies in the cochlear apex. In addition to a spatially selective processing of information along the cochlea, frequency information is conveyed by rate and phase lock. Phase lock in the pristine cochlea is up to 5 kHz. The loudness range is 120 dB with 60-100 discernable steps. In contrast to a normal hearing listener, a cochlear implant device divides the acoustical signal into less or equal to 22 frequency bands and can only parallel process 4 to 8 channels [27-30]. The limitation comes from the current spread in the cochlea, which leads to large sections of stimulation along the cochlea [31-37]. The delivery of the information is not precise, which is caused by the uncertain placement of the electrode [29, 38]. Shift of the frequency place, which can be caused by a, result in poor speech recognition [39]. The frequency range of a CI is typically limited 0.4 to 8 kHz. In particular, the inability of processing information below 0.4 kHz is crucial for speech recognition. Providing frequency information through phase lock is limited since phase lock in a CI is typically not more than 0.3 kHz. The loudness range is reduced to 6 to 30 dB with about 20 discernable steps [40].

Temporal Envelope (TE) and Temporal Fine Structure (TFS) are Both Important to Recognize Speech, Distinguish Speech in Noise, and for Music Appreciation.

Sinusoidal signals are used as standard stimuli for auditory research. The stimuli are well defined regarding their frequency, amplitude and timing. This makes it convenient for data analysis for two factors: (1) the cochlea is treated as a frequency analyzer and (2) linear system analysis can be applied. However, the cochlea is a highly nonlinear system, which processes complex natural sounds for communication. In general, acoustical signals can be decomposed into a slowly varying temporal envelope (TE, FIG. 1) and a rapidly varying temporal fine structure (TFS, FIG. 1) close to the center frequency of a given frequency band. The inner ear of a normal hearing subject or animal makes this decomposition. The cochlea then encodes TE by a rate-place code and TFS by a temporal code [45-57]. While psychophysical experiments demonstrated that both TE and TFS are important for performance in normal hearing subjects, it is still debated whether for hearing restoration with cochlear implants both components must be equally considered [41, 58-62]. This is of particular interest because, from a theoretical point of view, the TE can be recovered from TFS and vice versa [42-44].

Temporal Envelope (TE):

Similar to a frequency analyzer, the basilar membrane of the cochlea "separates" the frequencies contained in an acoustical signal into small frequency bands and maps the energy of each band to a fixed site along the cochlea. The acoustic energy of each frequency band is converted into a corresponding rate of action potentials of an auditory nerve fiber. The TE of a few spectral bands provides sufficient information for speech intelligibility in quiet [59, 63, 64].

Temporal Fine Structure (TFS):

In contrast to TE, the TFS of the acoustical signal plays an important role when speech is presented against a complex background noise [65-69] and for music perception. In the auditory nerve, TFS is encoded by phase-locked responses. At present, TFS is greatly neglected in CI coding strategies, which rely mostly on the envelope of the acoustical signal.

Evaluation of the Role of TE and TFS:

An elegant method to study the relative roles of TE and TFS are auditory chimaeras, which are acoustical constructs that have the TE of one sentence (or melody) and the TFS of another sentence (or melody). In quiet listening environments, speech constructed from two sentences is perceived as the sentence that provided the TE. This was different for music and for speech in noise. Instead, the stimulus that provided the TFS was recognized. Those experiments underline the importance of both TE and TFS for hearing [41]. Carefully designed experiments can be used to further our understanding of the role of TE and TFS in coding of acoustic parameters to enhance speech, speech in noise, and music recognition. One should also be aware that the approach with chimaeras has limitations because TE and TFS are not independent. TE can be recovered from TFS and vice versa. While in human testing it is difficult to tease apart true TFS and recovered TFS, this can be achieved in animal experiments where TFS is shown as a phase locked response of the nerve fiber.

At present, the temporal fine structure is greatly neglected and coding strategies rely solely on the temporal envelope of the acoustic signal. To better understand the arguments about the temporal envelop and the temporal fine structure, the terms are reviewed and techniques to implement them into coding strategies of CIs are discussed below.

Most of the information on which speech recognition is based is contained in the frequency band between 0 and 4000 Hz. For example, high-grade telephone channels have typically a channel capacity of 20,000 bits/s. If English phonemes are tabulated together with the probability of occurrence the average information per phoneme is 4.9 bits/s. In conversation about 10 phonemes are uttered per second. Consequently, about 50 bits/s of channels capacity would be sufficient to convey the information at the written equivalent of speech.

Basic Consideration for Coding Strategies:

Different strategies for coding acoustical information are shown in FIG. 2. The solutions depicted in panels A and B of FIG. 2 are not practical for cochlear implants and are presented for completeness. A train of biphasic pulses with constant amplitude (ca) and constant frequency (cf) has limited use because only single amplitudes can be encoded by the amplitude of the pulses and one single frequency by the pulse repetition rate (panel A of FIG. 2) or the stimulation site along the cochlea. Additional timing information can be added if the times are considered at which the carrier of the acoustical signal has zero crossings and the slope of the carrier is positive (panel B of FIG. 2). The TE of the acoustical signal can be used to modulate a constant carrier (panel D of FIG. 2). To avoid simultaneous stimulation at neighboring electrodes the carrier pulses are presented at adjacent electrodes in a continuous interleaved pattern (CIS) [71]. The latter strategy is commonly used in coding strategies of contemporary CIs. Some codes adopt the approach shown in panel E of FIG. 2. A carrier is amplitude modulated with the TE of the acoustical signal. The zero crossings of the TFS are then used to provide additional timing information. Coding strategies depicted in panels C and F of FIG. 2 have not been implemented in CI today. TFS is also included in the n-of-m coding strategy (n number of frequencies are selected of m possible frequencies) and by implementing virtual channels (stimulation between two electrode contacts by electrical field superposition). Current steering increases the number of possible frequencies that may be selected [72-75]. The n-of-m coding strategy can be seen as an alternative to CIS [76-78].

Nie and coworkers have proposed a coding strategy depicted in panel F of FIG. 2 [69, 79, 80], which encodes both amplitude and frequency of the signal. They suggest dividing the acoustical signal into frequency bands and extracting the temporal envelop, as has been done before. They suggest to also encode the frequency fine structure in each frequency band. Their test with CI user demonstrated, as others have before that TE, is sufficient to encode speech in quiet listening environments. They have also demonstrated that adding fine structure to the code can significantly improve speech recognition scores in normal hearing subjects when background noise is present [69, 79, 80].

While the temporal envelope is used in contemporary CI coding strategies, the temporal fine structure receives little attention.

In general, CI coding strategies accomplish three tasks: the extractions of the relevant information from the acoustical stimulus, the conversion of that information into an electrical stimulus, and the delivery of the stimuli via the cochlear implant electrode to the ear. Step one includes the filtering of the acoustical signal with pre-emphasis filter, dividing the acoustical signal into individual frequency components using filters, gammatone like filters, or spectrograms. From each frequency band the TE and TFS are extracted. In step two, different strategies are employed to select a few number of frequency bands. Typical strategies for this task are F0F1F2, multi peak (MPEAK), spectral peak (SPEAK), advanced combination encoder (ACE), n-of-m, fine structure processing (FSP). The TE of the selected frequency band is then used to modulate the amplitude of a carrier. The carriers are trains of biphasic electrical pulses delivered at a fixed rate. Different carriers have been tested: sinusoids, broad-band noise, narrow band noise and pulse trains with fixed and variable pulse rates. Typically, a nonlinear mapping function is applied. TFS is largely ignored in this process. In the third step, pulses are delivered via the CI electrode. If pulses occur at the same time at neighboring electrodes, interactions are possible. To avoid deleterious effects, two strategies are applied, current steering and CIS [62, 81]. Current steering uses the interaction between two neighboring channels to evoke a percept, which is between the sites of the electrodes used to deliver the current. This strategy increases the number of pitches a CI user can perceive [72]. CIS introduces delays between the pulses delivered at neighboring channels. The delays are large enough that simultaneous stimulation does not occur [71].

Five coding strategies, HiRes120, n-of-m, FSP, ACE, and SPEAK from three major cochlear implant companies, Advanced Bionics, Med-El and Cochlear Ltd., were analyzed to determine whether TFS is included in the CI coding strategy and how it is implemented. For two strategies, HiRes120 and n-of-m, both filter the acoustical signal captured by the microphone using a sequence of 16 bandpass filter ($6^{th}$ order Chebyshev with 3 dB ripple). They map the energy in each frequency band with a nonlinear function and generate trains of interleaved biphasic pulses with a high stimulation rate. The goal of the HiRes120 strategy is to increase temporal and spectral resolution and consequently introduce TFS [82-92]. To achieve the required higher spectral resolution, filtered signals from each channel are analyzed by using the FFT of the signal to select maxima that represent dominant frequency components. If selected frequencies are within the resolution band of a patient, the one with smaller magnitude is eliminated. The resolution band is the frequency range where patients could not distinguish pitch differences and is set as ⅓ octave in the HiRes120 code. Current steering is then used to stimulate the corresponding sites along the cochlea. The stimulation sites are determined by using the selected frequencies and the Greenwood function [93], which maps the frequencies tonotopically along the cochlea. Furthermore, to achieve better timing resolution, this strategy also uses the half-wave rectified waveform to modulate the electrical pulse trains [94]. The n-of-m strategy differs only in the criteria of selecting channels. A threshold is determined by calculating the average energy of all channels [95]. The energy of each channel is then subtracted by the threshold value and the difference d is used to calculate a probability p. Each channel is assigned with a random number r within [0,1], which is then compared with p accordingly. In case that r is less than p, then the channel is selected. After testing all channels, if the number of selected channels is smaller than 6, then unpicked channels are randomly selected until all six channels are selected. If the number of channels is larger than 6, picked channels are randomly deselected until six channels remain. The threshold is also adjusted accordingly [96].

Another coding strategy that considers TFS uses a combination of a High Definition CIS (HDCIS) strategy for high frequencies (electrode contacts at the basal cochlear end) and channel-specific sampling sequences (CSSS) at one to four most apical channels or electrode contacts. The channel selection is based on the finding that only neurons at low frequency signal (<1 kHz) phase lock in severe-to-profound hearing impaired, and hence respond to TFS. The filters used in this strategy are a series of bell curve shaped bandpass filters with overlap at −3 dB cutoff frequencies [97]. This can be achieved with a gammatone filter. The frequency range is 70 to 8000 Hz, separated into 12 channels. At the high frequency channels, the signals are Hilbert transformed to extract the TE. The TE obtained at each channel is then used to modulate the amplitude of a carrier (sequence of interleaved biphasic pulses at a rate of about 1500 pulses per second (pps)). At the low frequency channel, TFS is encoded. The acoustical signal are half-wave rectified such that only positive values remain. Positive zero points, which are points with zero value and positive derivatives on the waveforms, are identified from rectified signals and marked as the time point to generate pulse trains using the CSSS strategy. The rate of pulse trains is fixed and patient specific. This method gives a non-constant rate of stimulation among apical channel, where length of the pulse bursts depends on the center frequencies. This approach provides TFS information of the acoustical signal [98].

Two other common coding strategies do not introduce TFS and rely on TE only. In the ACE strategy, a pre-emphasis filter with a shape of equal loudness threshold among frequencies is used. The goal is to emulate the "perceptual power" similar to what normal hearing people perceive. Next, the signal is analyzed by two spectrograms: one with 256 points window size, which has better spectral resolution, and one with 64 points window size, which has better time resolution. Both spectrograms are vocoded to 22 channels. The "256-window" spectrogram is mainly used as the criteria for channel selection. In this strategy, 8 channels with highest energies are selected. After the channel is selected, the two adjacent channels are checked to see if the energy differences are below the threshold limit, defined as 20 dB less energy than the selected channel. If the energy is below the threshold limit, then that channel is considered to be masked by the selected channel and should be eliminated from proceeding channel selections [99]. Once all 8 channels are selected, energy derived from "64-window" spectrogram is considered as the stimulation power for each selected channel. Similar to strategies described above, energies are mapped to current levels and pulses are delivered as interleaved biphasic manner at a high stimulation rate (2500 pps) [100].

The other method, SPEAK, is a low pulse repetition rate coding strategy. The pre-processed signal is analyzed with a 256 points window size spectrogram and then vocoded to 22 channels. A gain factor G is calculated for each channel every 3 frames (48 ms) using the following function: G=(2×

$E_c-2-E_p-E_f)/(E_c+E_p+E_f)$, where $E_c$, $E_p$ and $E_f$ are energy of the first, second and third frame. G describes how fast the envelope energy varies, and emphasizes the transients of the speech signal where envelope changes quickly. G must be larger than zero and smaller than 2. A modified signal S' is then computed using S'=S×(1+K×G), where S is the original signal and K is the modifier constant with value of 2 [41, 101]. Eight channels with the highest energies are selected and the pulse amplitudes are mapped to current levels [102]. The method of delivering pulses in this strategy is different. Either a pulse burst, which is a sequence of ramping pulses [103], or a ±10% jitter of the pulse timing can be used [104]. Both methods aim to introduce stochastic time patterns of neural activity.

A coding strategy has been described by Nie et al. [69] that considers TE and TFS. Algorithms for extracting AM and FM. The acoustical signal is divided into N subbands by a bank of bandpass filters. Within each subband, amplitude and frequency modulations are extracted in separate pathways. The output of each subband k is full-wave rectified and then filtered with a low pass to obtain the AM signal. Delay compensation is also introduced to synchronize the amplitude and frequency modulation pathways. A pair of orthogonal sinusoidal signals at the center frequency of the k th subband is used to remove the center frequency from the original signal and to extract frequency modulation around the center frequency. The resulting signal is Low-pass filtered. The instantaneous frequency is calculated from the in- and out-phase signal. The instantaneous frequency is further band-limited and low-passed filtered to limit the frequency modulation rate. However, two problems limit the use of the approach described: (1) the trains of pulses are still amplitude modulated and increasing current amplitudes results in in increasing interactions between neighboring electrodes. (2) frequency modulation is retrieved from each subband and used to modulate the spike patterns. Additionally, this approach does not take into account the phase information.

Therefore, a heretofore unaddressed need exists in the art to address the aforementioned deficiencies and inadequacies.

SUMMARY OF THE INVENTION

In one aspect, the invention relates to a method of generating frequency-modulated electrical pulse trains in a cochlear implant. In one embodiment, the method comprises the steps of dividing data representing audio spanning a plurality of frequency bands into a plurality of bins associated with each of the frequency bands, each bin representing an energy level of the audio data within the frequency band within a period of time; associating each frequency band with a phase probability that starts at an initial phase probability value, resets to a minimum phase probability value after a pulse is generated, and increases from the minimum phase probability value to a maximum phase probability value over a period of time; for each bin, assigning a power probability as a normalized intensity for each bin, the normalized intensity being a number between a minimum power probability and a maximum power probability representing the energy level of the bin; and for each bin, generating a pulse in an electrode associated with the frequency band associated with the bin when a random number generated is less than the power probability divided by the phase probability.

In one embodiment, a pulse rate in the electrode associated with the frequency band associated with the bin varies between zero pulses per second and a maximum pulses per second.

In one embodiment, the minimum power probability is 0. In one embodiment, the maximum power probability is 1.

In one embodiment, the period of time is equal to one divided by a center frequency of the frequency band.

In one embodiment, the initial phase probability value is equal to the maximum phase probability value.

In one embodiment, the initial phase probability value is 1.

In one embodiment, the minimum phase probability value is 0. In one embodiment, the maximum phase probability value is 1.

In one embodiment, the phase probability increases linearly. In another embodiment, the phase probability increases according to a Gaussian function.

In one embodiment, the number of frequency bands corresponds to the number of electrodes in the cochlear implant.

In one embodiment, the random number generated is a random number between a minimum modified power probability and a maximum modified power probability; the minimum modified power probability defined as a smallest possible value of the power probability divided by the phase probability and the maximum modified power probability defined as a largest possible value of the power probability divided by the phase probability.

In one embodiment, the minimum modified power probability is 0. In one embodiment, the maximum modified power probability is 1.

In another aspect, the invention relates to a cochlear implant providing frequency-modulated electrical pulse train. In one embodiment, the cochlear implant includes a plurality of electrodes; and a processor in communication with the plurality of electrodes, the processor generating frequency-modulated electrical pulse trains in one or more of the plurality of electrodes in response to dividing data representing audio spanning a plurality of frequency bands into a plurality of bins associated with each of the frequency bands, each bin representing an energy level of the audio data within the frequency band within a period of time; associating each frequency band with a phase probability that starts at an initial phase probability value, resets to a minimum phase probability value after a pulse is generated, and increases from the minimum phase probability value to a maximum phase probability value over a period of time; for each bin, assigning a power probability as a normalized intensity for each bin, the normalized intensity being a number between a minimum power probability and a maximum power probability representing the energy level of the bin; and for each bin, generating a pulse in an electrode associated with the frequency band associated with the bin when a random number generated is less than the power probability divided by the phase probability.

In one embodiment, a pulse rate in the electrode associated with the frequency band associated with the bin varies between zero pulses per second and a maximum pulses per second.

In one embodiment, the period of time is equal to one divided by the center frequency of the frequency band.

In one embodiment, the initial phase probability value is equal to the maximum phase probability value.

In one embodiment, the phase probability increases linearly, or increases according to a Gaussian function.

In one embodiment, the number of frequency bands corresponds to the number of electrodes in the cochlear implant.

In one embodiment, the random number generated is a random number between a minimum modified power probability and a maximum modified power probability; the minimum modified power probability defined as a smallest possible value of the power probability divided by the phase probability and the maximum modified power probability defined as a largest possible value of the power probability divided by the phase probability.

In another aspect, the invention relates to a non-transitory computer-readable medium storing instructions which, when executed by one or more processors, cause a cochlear implant to perform a method for generating frequency-modulated electrical pulse trains in one or more of a plurality of electrodes of the cochlear implant. The method comprises dividing data representing audio spanning a plurality of frequency bands into a plurality of bins associated with each of the frequency bands, each bin representing an energy level of the audio data within the frequency band within a period of time; associating each frequency band with a phase probability that starts at an initial phase probability value, resets to a minimum phase probability value after a pulse is generated, and increases from the minimum phase probability value to a maximum phase probability value over a period of time; for each bin, assigning a power probability as a normalized intensity for each bin, the normalized intensity being a number between a minimum power probability and a maximum power probability representing the energy level of the bin; and for each bin, generating a pulse in an electrode associated with the frequency band associated with the bin when a random number generated is less than the power probability divided by the phase probability.

In one embodiment, a pulse rate in the electrode associated with the frequency band associated with the bin varies between zero pulses per second and a maximum pulses per second.

In one embodiment, the period of time is equal to one divided by the center frequency of the frequency band.

In one embodiment, the initial phase probability value is equal to the maximum phase probability value.

In one embodiment, the phase probability increases linearly, or increases according to a Gaussian function.

In one embodiment, the number of frequency bands corresponds to the number of electrodes in the cochlear implant.

In one embodiment, the random number generated is a random number between a minimum modified power probability and a maximum modified power probability; the minimum modified power probability defined as a smallest possible value of the power probability divided by the phase probability and the maximum modified power probability defined as a largest possible value of the power probability divided by the phase probability.

According to the invention, the coding strategy/method to encode acoustical information in cochlear implants has, among other things the advantages over existing coding strategies relate to the following points:

1. Auditory nerve stimulation can be done simultaneously at all contacts of the electrode array and increases the number of independent channels from 4 to up to 22.

2. Average pulse repetition rates are about 100-300 Hz at each channel.

3. Loudness is encoded by the number of pulses in each channel and the total number of pulses across channels and does not require the increase in current level for each channel.

4. The low average pulse repetition rate for each channel and the fact that loudness increase is not coded through an increase in current amplitude reduces the power consumption of the devices by a factor of about 5 to 10.

5. Phase is added to the pulse pattern, which communicates temporal fine structure.

For the coding strategy according to the invention, the acoustic signal is received using a microphone or the like. A series of filters extracts the acoustic information in up to 22 frequency bands. A Short Term Fourier Transform (STFT) is applied to the traces of each frequency band to extract the envelop of the signal over time. For each frequency band, a pulse generator generates trains of pulses with random times between the pulses while the average pulse rate is varied and proportional to the extracted envelope. Since stimulation occurs at each channel, a frequency selection strategy, such as used in the existing coding strategies, is not necessary.

These and other aspects of the invention will become apparent from the following description of the preferred embodiment taken in conjunction with the following drawings, although variations and modifications therein may be affected without departing from the spirit and scope of the novel concepts of the invention.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

FIG. 7A shows the spectrogram of the sentence "The boy did a handstand", where a pre-emphasis filter was applied, and FIG. 7B shows the pulse pattern for this sentence, where each circle shows the time of an electric biphasic pulse. Note that pulses can be delivered simultaneously at neighboring channels. Based on the slow pulse repetition rate and the stochastic behavior of the pulses, however, coincident events at neighboring electrodes are rare.

FIGS. 8A-8E show a relationship of a normalized rate of action potentials that can be recorded at a single auditory nerve fiber and a sound level at the outer ear canal to a rate for different parameters $a_0$, $a_1$, $a_2$, $a_3$, $a_4$.

FIG. 10 is a table listing demographics of tested participants/patients.

FIG. 11 is a table illustrating comparison of performance with the FMPC according to embodiments of the present invention and performance with the Med El or AB processing code.

FIGS. 14A-14C are tables listing the data obtained in the individual sessions according to embodiments of the present invention.

FIG. 20 is a table listing the corresponding values of the pulse patterns of FIGS. 19A-19D.

FIG. 21 is a table listing answers of a yes-no questionnaire of the participants.

FIG. 22 is a table listing preliminary results of a music test according to embodiments of the present invention.

DETAILED DESCRIPTION OF THE INVENTION

Figure 1:
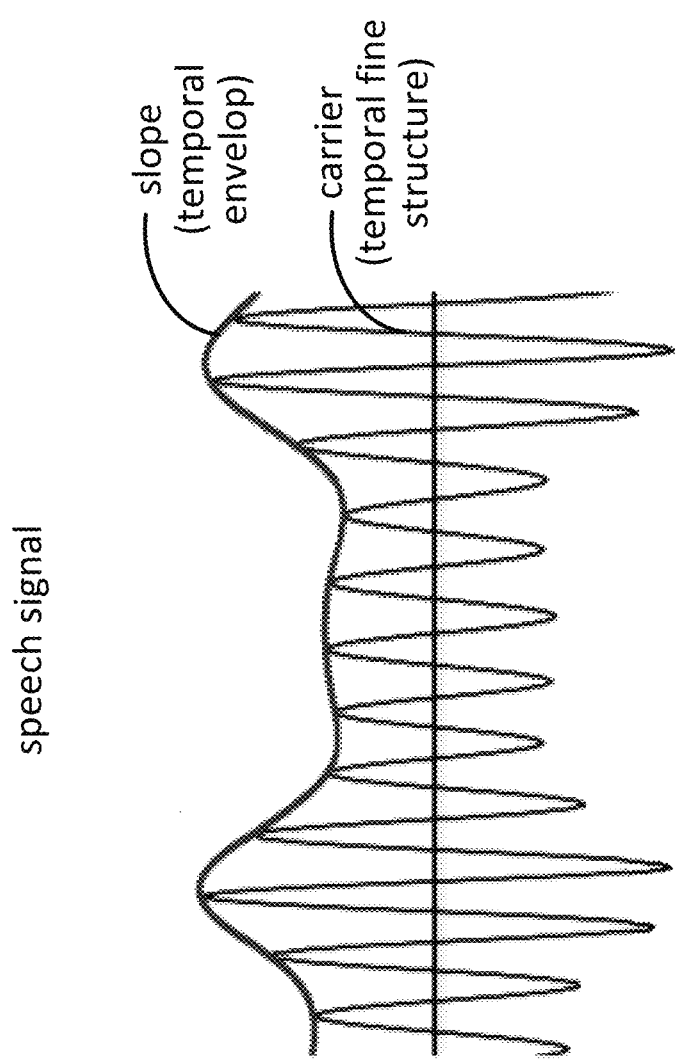
FIG. 1 shows schematically an acoustic signal comprising a slow changing envelope (a temporal envelope or slope) and a fast changing component (a temporal fine structure or carrier). The temporal envelope and the temporal fine structure are able to independently convey acoustic information. While the temporal envelope has been shown to be important for speech in quiet, the temporal fine structure is important for music and speech in noise.
Figure 2:
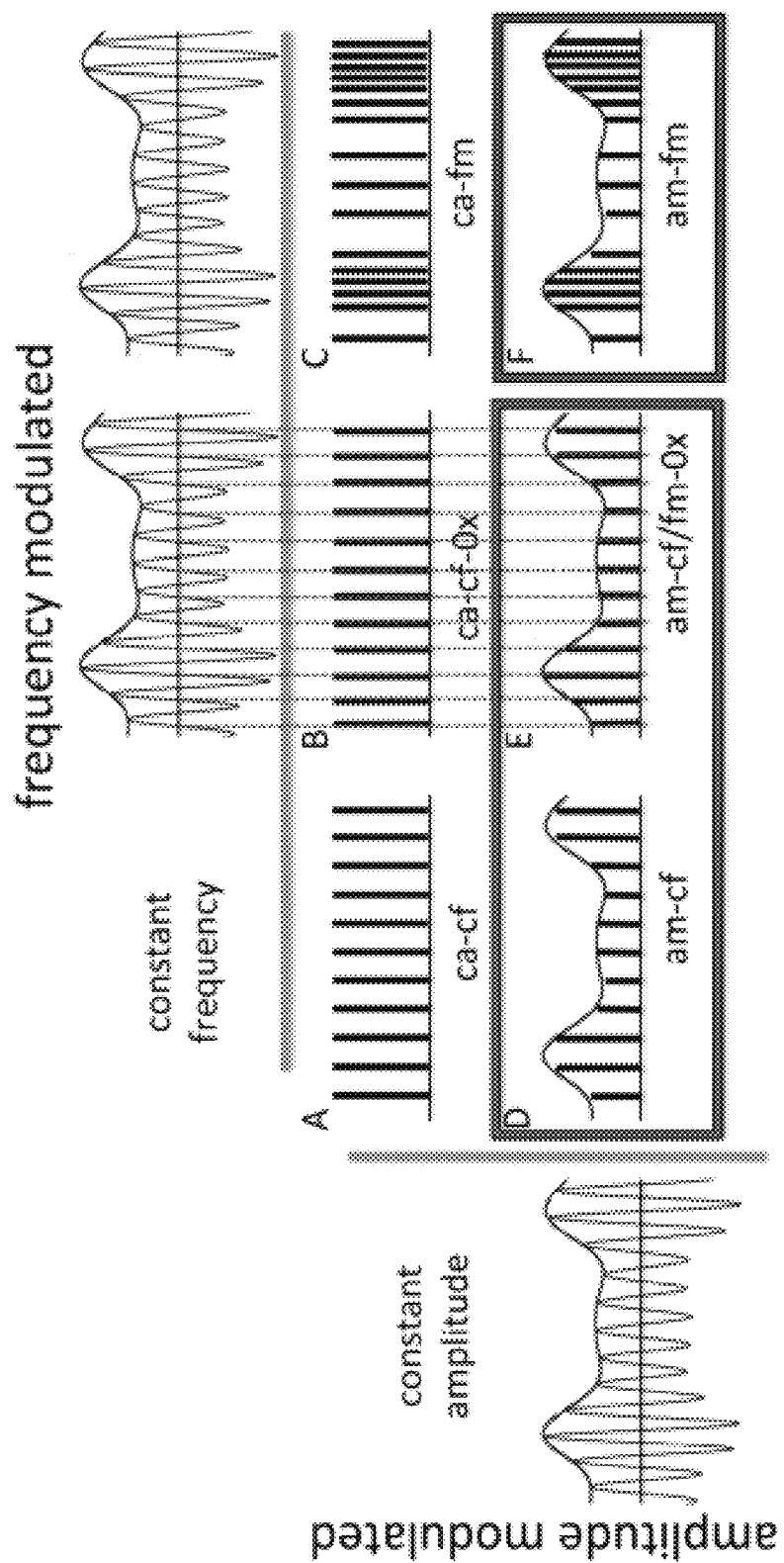
FIG. 2 shows schematically different strategies for coding acoustical information, where abbreviations are ca=constant amplitude, cf=constant frequency, am=amplitude modulation, fm=frequency modulation, 0x=zero crossings. Contemporary coding strategies can mostly be described by the paradigms in panels D and E, where the carrier is fixed in rate, and the pulse trains are amplitude modulated. A few coding strategies consider the zero crossing to add fine structure information in some of their channels. To encode the temporal envelope and the temporal fine structure, a code as shown in panel F is required.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that, as used in the description herein and throughout the claims that follow, the meaning of "a", "an", and "the" includes plural reference unless the context clearly dictates otherwise. Also, it will be understood that when an element is referred to as being "on" another element, it can be directly on the other element or intervening elements may be present there between. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising," or "includes" and/or "including" or "has" and/or "having", or "carry" and/or "carrying," or "contain" and/or "containing," or "involve" and/or "involving, and the like are to be open-ended, i.e., to mean including but not limited to. When used in this disclosure, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the phrase "at least one of A, B, and C" should be construed to mean a logical (A or B or C), using a non-exclusive logical OR. It should be understood that one or more operations within a method is executed in different order (or concurrently) without altering the principles of the invention.

As used herein, the term "action potentials" refer to the electric response of nerve fibers or muscle tissues to its stimulation such as electrical stimuli, optical stimuli, and/or acoustic click stimuli. The action potentials are considered as the traveling signals of nerves and the localized changes that contract muscle cells responsive to the stimulation. Compound action potentials are the summation of individual action potentials from single neurons.

As used herein, the term "nerve fiber" refers to a portion of the neuron, namely the axon, which carries action potentials from one end of the neuron to the other. The cochlear nerve fibers originate from neurons of the spiral ganglion and project peripherally to cochlear hair cells and centrally to the cochlear nuclei (cochlear nucleus) of the brain stem. They mediate the sense of hearing.

The term "cochlea", as used herein, refers to a spiral-shaped cavity of the inner ear that resembles a snail shell and contains nerve endings essential for hearing. The cochlea includes three fluid-filled chambers: scala tympani and scala vestibuli (both of which contain perilymph), and scala media (which contains endolymph). The scala tympani and the scala vestibuli are contiguous with each other, merging at the tip of the snail shell, the helicotrema. The stapes transmits vibrations to the fenestra ovalis (oval window) on the outside of the cochlea, which vibrates the perilymph in the scala vestibuli. This in turn vibrates the endolymph in the scala media, thus causing movements of the hair bundles of the hair cells, which are acoustic sensor cells that convert vibration into electrical potentials.

The term "cochlear implant" or its abbreviation "CI", as used herein, refers to a device that is placed into the cochlea to provide sound perception for deaf individuals.

Embodiments of the invention are illustrated in detail hereinafter with reference to accompanying drawings. It should be understood that specific embodiments described herein are merely intended to explain the invention, but not intended to limit the invention. In accordance with the purposes of this invention, as embodied and broadly described herein, this invention, in certain aspects, relates to coding strategies for cochlear implants (CIs) and cochlear implants applying the same.

According to the present invention, the frequency-modulated phase coding (FMPC) strategy to encode acoustical information in cochlear implants does not modulate the amplitude, but uses the amplitude to calculate the spike probability. At high energy levels the probability that a pulse is generated is high and fast pulse repetition rates result. At low sound energy levels, the probability for a pulse is low and the resulting pulse repetition rate is slow. In addition to the sound energy the phase is considered in the calculation. The probability for a pulse is maximum at integer times corresponding to the center frequency of the selected frequency band and is close to zero at the other times. Thus, TE is encoded by the rate and TFS is recovered from the TE of the acoustical signal and the center frequency of the selected sub-band.

As discussed above, only two of the five existing coding strategies claim efforts to implement TFS. The other strategies rely on the limited frequency information provided by the TE. Also, some of the TFS can be "recovered" from TE [42, 105, 106]. In contrast to the CI processors' coding strategies, the auditory system of a normal hearing animal/human encodes TE and TFS at the same time. TE is determined by the sound induced vibrations of the basilar membrane, which have a maximum at a specific site along the cochlea for each frequency; TFS is encoded by the fast oscillations of the basilar membrane (e.g., [57, 60, 62, 69, 105]). Recordings of neural activity from single auditory nerve fibers have been taken to characterize the neural responses to simple stimuli, such as pure tones. Important information of how amplitude and frequency information is encoded by the auditory system has been gained from those studies [54, 55, 107-113]. Efforts have also been undertaken to describe the response patterns of single auditory nerves to natural sounds including simple speech [114-121]. The results clearly demonstrate that the response strength depends on the best frequency of the neuron and the stimulus frequency. When the neuron responds to a simple speech signal, it will respond in particular to the intrinsic primary frequencies [117, 118, 121, 122]. The data show that if the characteristic frequency of the neuron is close to the dominant component it will better respond to the stimulus. However, the neuron will also respond to other components.

Validation from Animal Experiments that the Temporal Fine Structure is Important in Neural Coding.

Figure 3:
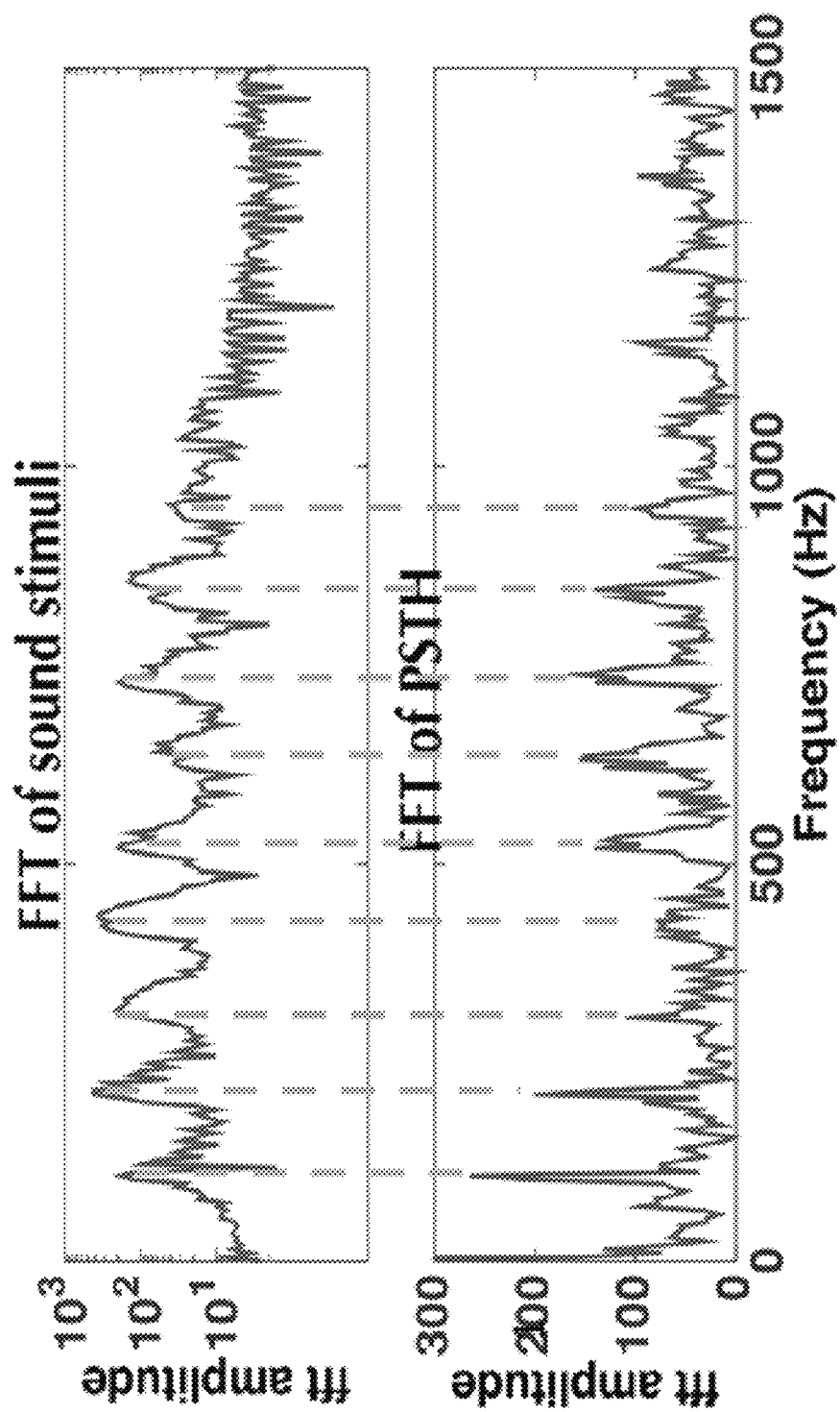
FIG. 3 shows a spectral plot of the acoustic stimulus (top) and the PSTH (bottom) from a stable single unit in the ICC (CF=2500 Hz). The unit phase locks to the intrinsic primary frequencies from the sounds. The phase locking pattern to complex sounds is heavily mediated by frequency components of sounds and the sound levels.

Experiments were conducted in guinea pigs to address whether phase information is maintained in the midbrain, and whether it can be extracted if complex sounds, like running speech, are presented to the outer ear canal. Neural activity was recorded from stable units in the central nucleus of the inferior colliculus (ICC). The neuron was characterized by analyzing the neural activity obtained during stimulation of the cochlea with single pure tones at the characteristic frequency of the neuron, complex tones comprised of the fundamental frequency in the acoustic signal and the formants f1-f3 and their harmonics and to natural sound such as running speech. The response to a short sentence is shown in FIG. 3. To examine phase locking of the neural response, a post stimulus histogram (PSTH) of the neural responses to 300 stimulus repetitions was constructed, and the Fast Fourier Transform of the PSTH (see FIG. 3, lower panel) was examined. By comparing the FFT obtained from the acoustic stimulus (FIG. 3, upper panel) with the results from the PSTH (FIG. 3, lower panel) it can be seen that the units in the ICC phase lock to the frequencies in the acoustical signal if their component was below 1 kHz. This finding is independent of the CF of the unit as long as it is sensitive enough to be activated by the energy in a dominant frequency band in the stimulus. The results are similar to what has been demonstrated in single auditory nerve fibers [117-121].

Distortion of the Temporal Fine Structure Compromises Speech and Speech in Noise Recognition (Normal Hearing Subjects).

The contribution of TFS was evaluated on speech recognition in normal hearing human test subjects. Speech was modified by keeping the TE unaltered and by changing the TFS through modifying the phase information. Speech tests were given at different signal to noise ratios (SNR).

Figure 4:
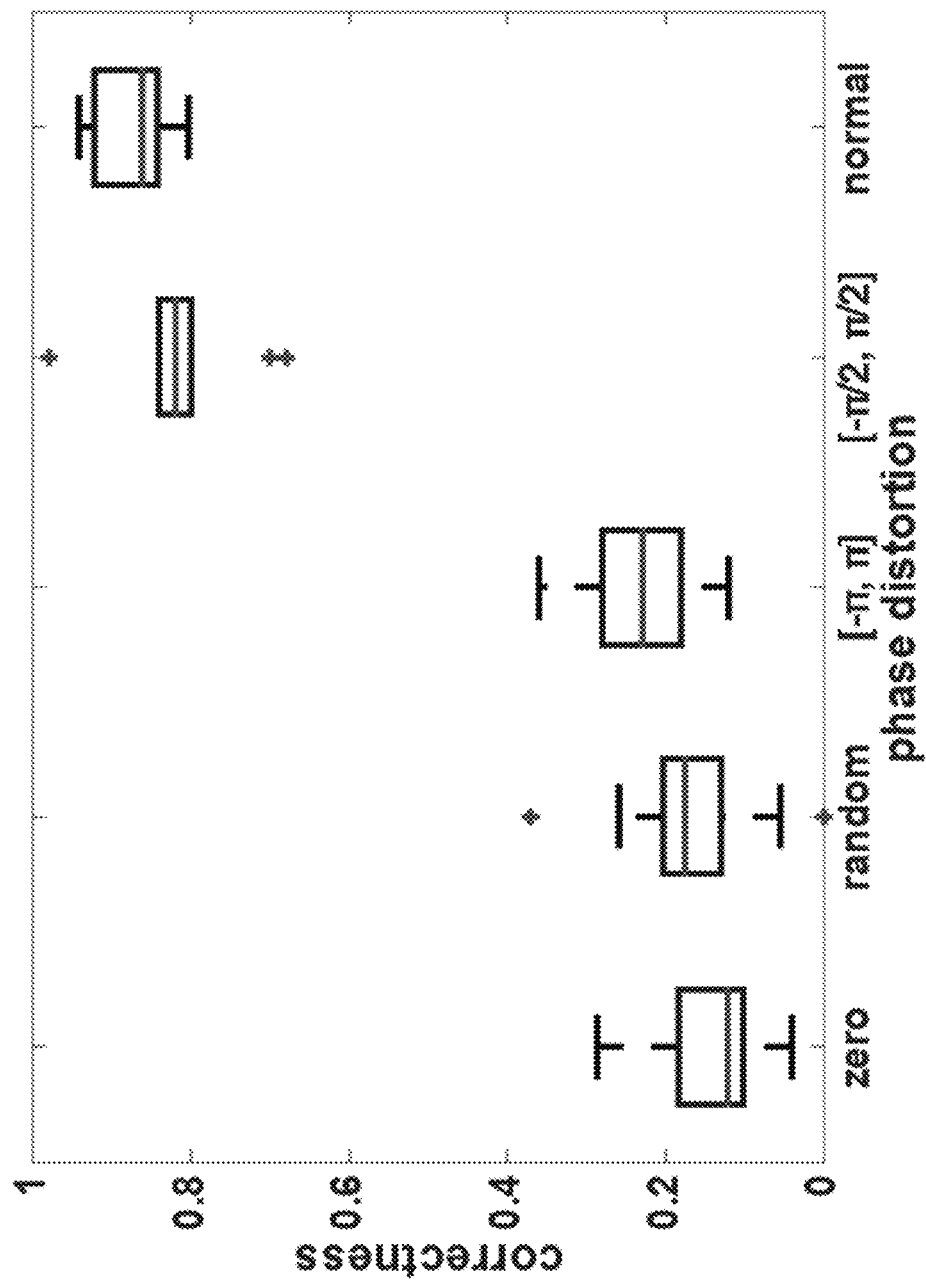
FIG. 4 shows a relationship of a speech recognition correctness and a phase distortion. Speech recognition scores are significantly decreased with distorted phase information such as zero, random or shifted phase. Differences in speech recognition scores are statistically significant between random phase and randomly distributed around the original phase ($\pi_0$), [$\pi_0-\pi$, $\pi_0+\pi$] (p-value=0.031<0.05), and between [$\pi_0-\pi$, $\pi_0+\pi$] and [$\pi_0-\pi/2$, $\pi_0+\pi/2$] (p-value=0<0.05). Speech is unintelligible when a zero or random phase replaces the original phase ($\pi_0$), with a slight improvement at [$\pi_0-\pi$, $\pi_0+\pi$], and significant improvement for [$\pi_0-\pi/2$, $\pi_0+\pi/2$] phase shift or with the original phase ($\pi_0$), when reconstructing sound.

Results obtained for each of the phase distortions are shown as box plot in FIG. 4. An analysis of variance was performed. The Tukey's honest significance test was used for pairwise comparison. The results show that speech is unintelligible when the phase is set to a fixed value, here zero, or when the phase is randomly assigned. A drastic improvement in speech intelligibility can be seen if the range over which the phase is randomly assigned is decreased from $[-\pi,\pi]$ to $$[-\frac{\pi}{2}, \frac{\pi}{2}].$$

Figure 5:
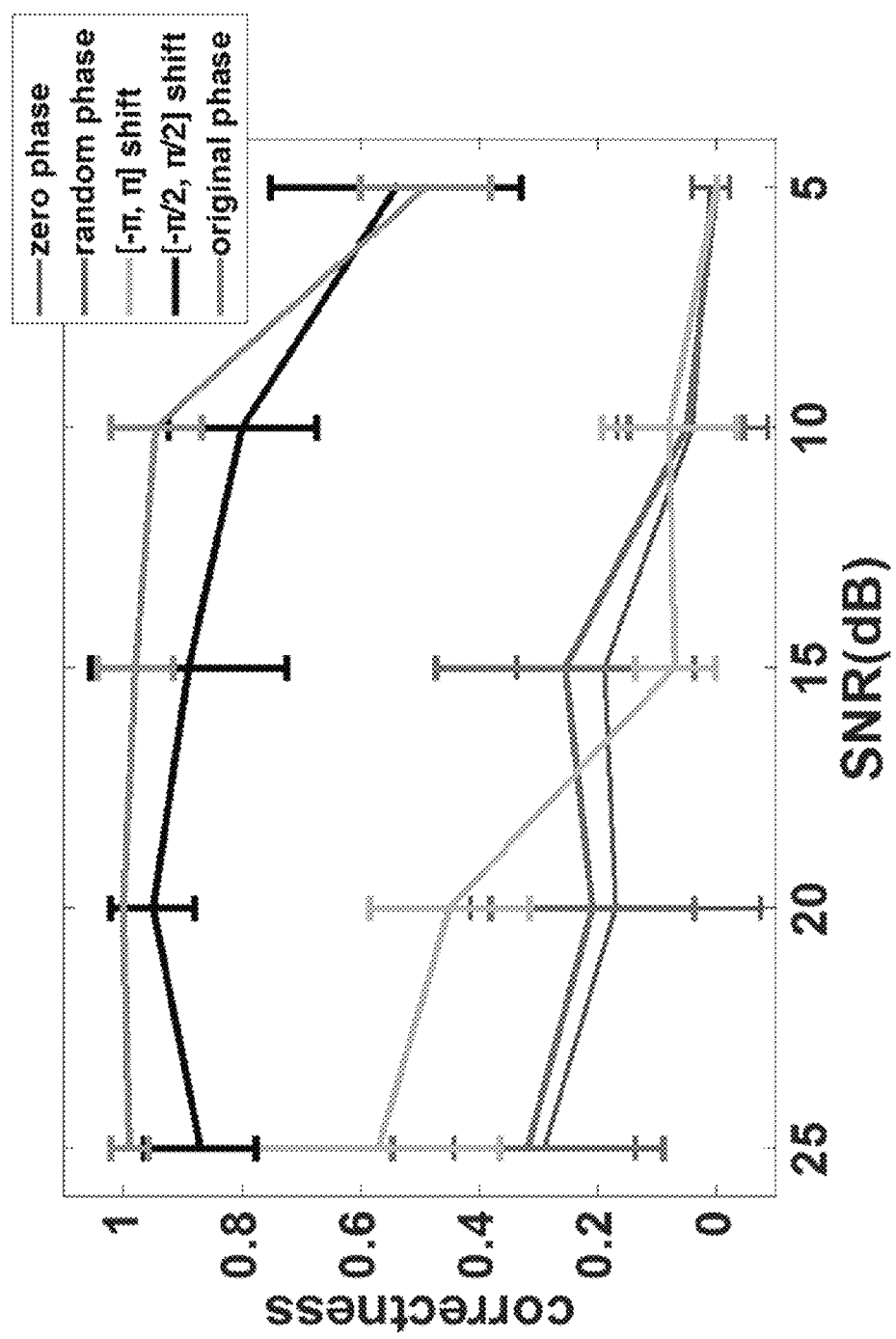
FIG. 5 shows a relationship of a speech recognition correctness and a signal-to-noise-ratio (SNR). Speech recognition scores significantly decrease with distorted phase information such as zero, random or randomly distributed around the original phase ($\pi_0$), [$\pi_0-\pi$, $\pi_0+\pi$], and [$\pi_0-\pi/2$, $\pi_0+\pi/2$]. Speech recognition scores decrease with increasing background noise, shown in the plot as a decreasing SNR. The plots clearly demonstrate that the phase information is crucial in particular for the speech recognition in noise. For a normal hearing subject, the speech recognition is close to zero if the SNR is less than 15.

The percent correct increased from about 20% to about 80%. The importance of the phase or the TFS is also important for speech in the noise recognition, as shown in FIG. 5. For the original phase or if the phase is randomized in $$[-\frac{\pi}{2}, \frac{\pi}{2}]$$

the scores from the speech recognition test are 80% correct if the SNR is 10 dB or above. For the other phase randomized conditions the scores decreased from about 50% (SNR=25 dB) to 20% (SNR=15 dB). For a SNR<10 dB, the speech recognition scores are close to 0%.

FREQUENCY-MODULATED PHASE CODING (FMPC)

Figure 6A:
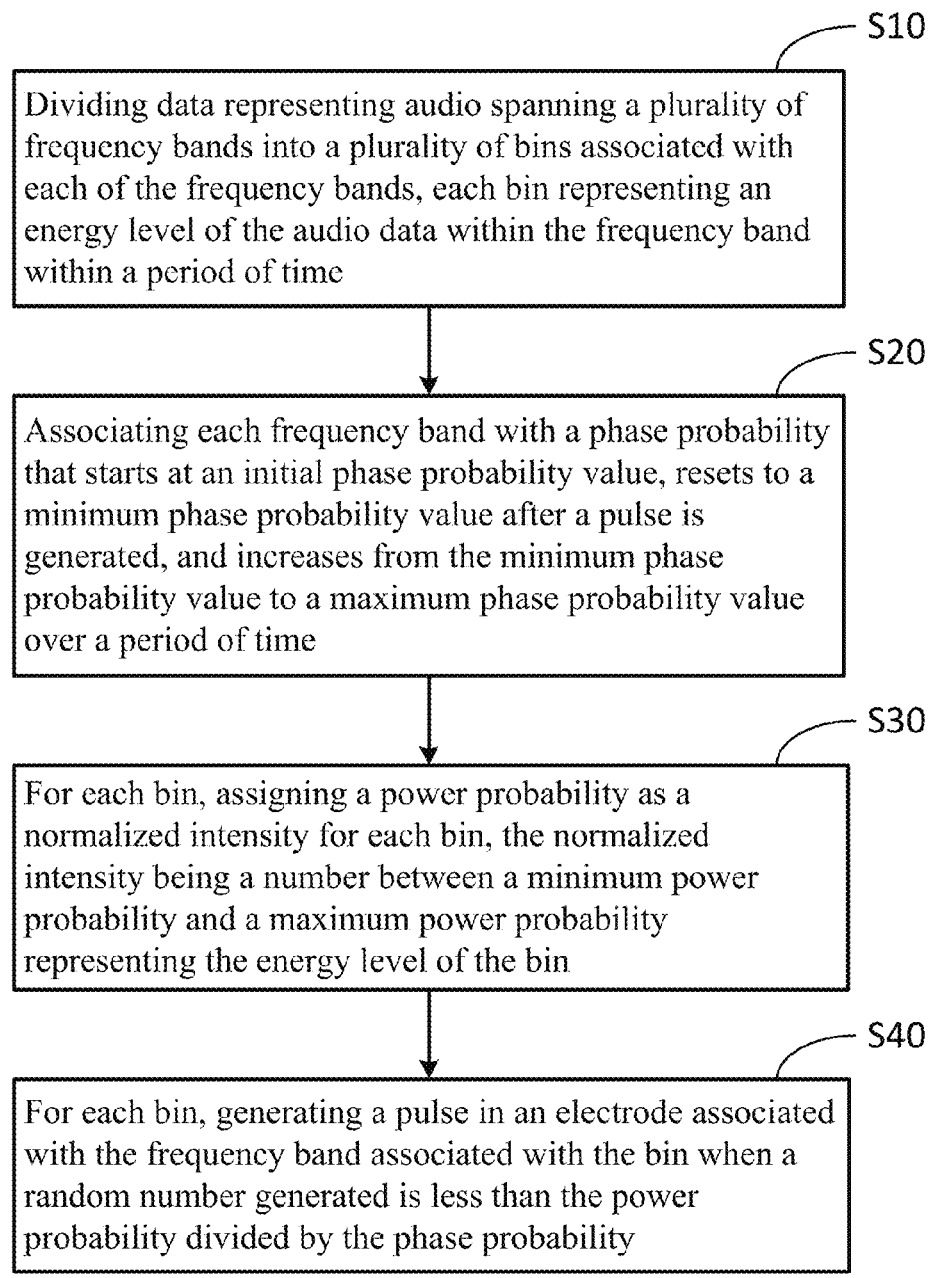
FIGS. 6A and 6B show a flow chart for encoding of acoustic information with a frequency-modulated phase coding (FMPC) strategy according to embodiments of the present invention.

Referring to FIG. 6A, a flow chart for a method of generating frequency-modulated electrical pulse trains in a cochlear implant, i.e., frequency-modulated phase coding (FMPC) for a cochlear implant, is shown according to one embodiment of the present invention. As shown in FIG. 6A, the method generally includes the following steps.

At step S10, data representing audio spanning a plurality of frequency bands is divided into a plurality of bins associated with each of the frequency bands. Each bin represents an energy level of the audio data within the frequency band within a period of time. The audio (acoustical) signal can be captured with a microphone or a recorder, or provided as an audio file. In certain embodiments, the number of the plurality of frequency bands corresponds to the number of electrodes in the cochlear implant. The period of time is equal to one divided by a center frequency of the frequency band, i.e., 1/(center frequency).

At step S20, each frequency band associated with a phase probability that starts at an initial phase probability value, resets to a minimum phase probability value after a pulse is generated, and increases from the minimum phase probability value to a maximum phase probability value over a period of time.

In certain embodiments, the initial phase probability value is equal to the maximum phase probability value. In some embodiments, the initial phase probability value is 1.

In certain embodiments, the minimum phase probability value is 0. The maximum phase probability value is 1.

In one embodiment, the phase probability increases linearly. In another embodiment, the phase probability increases according to a Gaussian function.

At step S30, for each bin, a power probability is assigned as a normalized intensity for each bin. The normalized intensity is a number between a minimum power probability and a maximum power probability representing the energy level of the bin. In one embodiment, the minimum power probability is 0. In one embodiment, the maximum power probability is 1.

At step S40, for each bin, a pulse is generated in an electrode associated with the frequency band associated with the bin when a random number generated is less than the power probability divided by the phase probability. In one embodiment, a pulse rate in the electrode associated with the frequency band associated with the bin varies between zero pulses per second and a maximum pulses per second.

In some embodiments, the random number generated is a random number between a minimum modified power probability and a maximum modified power probability; the minimum modified power probability defined as a smallest possible value of the power probability divided by the phase probability and the maximum modified power probability defined as a largest possible value of the power probability divided by the phase probability. In some embodiments, the minimum modified power probability is 0, and the maximum modified power probability is 1.

Figure 6B:
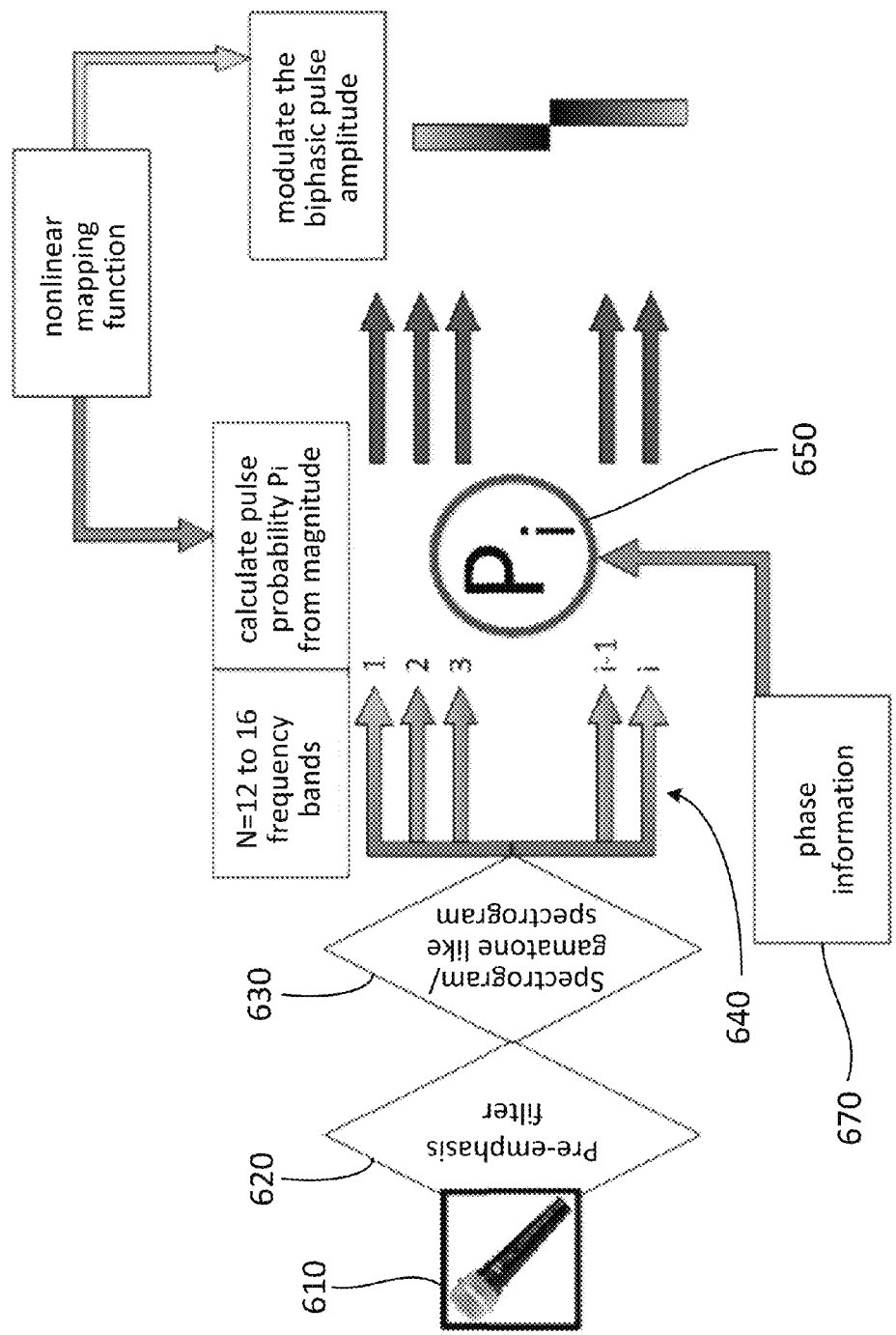

FIG. 6B shows a flow chart of the frequency-modulated phase coding (FMPC) strategy in another form. In this exemplary example, the acoustical (audio) signal is captured with a microphone 610. The audio signal can be acquired by a recorder or other audio acquiring devices, or provided as an audio file. A pre-emphasis filter 620 is applied to the input audio signal before a spectrogram or gammatone-like spectrogram 630 is calculated to decompose the audio signal into different frequency bands 640. For each frequency band, a probability 650 for an electrical pulse is calculated from the acoustic power in the audio signal, as reflected in the spectrogram or gammatone-like spectrogram 630. This probability 650 is further modified by the phase information 660 in the acoustic signal. In one exemplary example, 12 frequencies (i.e., 192, 301, 442, 626, 863, 1185, 1598, 2162, 2941, 3870, 5252 and 6684 Hz) were selected from the resulting spectrogram as shown in FIG. 7. The number of frequencies equals the active number of electrode contacts along the cochlear implant array. For example, for a Med-El device the number of frequencies is 12, for an Advanced Bionics Device the number of frequencies 16, and for a Cochlear Device the number of frequencies 22. The selection of the frequency band determines the rows of the spectrogram. In one embodiment, the frequency selection is achieved interactively with the patient. Initially the patient interacts with a computer to adjust an initial distribution of frequencies to the electrode contacts using an fast converging algorithm. After the initial adjustment, for each listening environment a fast adjustment is done upon prompting from the CI device. The resulting parameter set is stored and used to predict optimal parameter settings for the CI user. In one embodiment, parameter setting predictions are done using a Bayesian approach.

The magnitude in each row of the spectrogram is converted into a normalized rate, a number between 0 and 1. The normalized rate, which is also called a power probability, PowerProb, is then modified by dividing by a value of a phase probability, PhaseProb, of the interval $[0,1]*w_{phase}$, where the multiplier $w_{phase}$ is a factor that can increase or decrease the phase effect. For the initial setting this weighing factor $w_{phase}$ is selected to be 1. The resulting value obtained from dividing PowerProb and PhaseProb is then compared with a random number between 0 and 1 generated with a random number generator, for example, a MATLAB's random number generator, or the like. A pulse is generated if the random number is smaller than the number calculated from the normalized rate and the phase. A typical example for the spectrogram and the resulting electrical pulse pattern is shown in FIG. 7A for the sentence "The boy did a handstand". Each circle in the raster plot shown in FIG. 7B corresponds to the time of an electrical pulse to be delivered. The amplitude of the pulse may be modulated.

Intensity Mapping and Normalized Rate—Calculation of PowerProb:

In previous research, an equation was been proposed that describes the relation between the sound level at the outer ear canal and the corresponding rate of action potentials that can be recorded from a single auditory nerve fiber [123-128]. This function is expressed below and includes cochlear nonlinearities and depends on five critical parameters: a spontaneous rate ($a_0$), a maximum rate ($a_1$), a threshold for stimulation ($a_2$), a level for nonlinear behavior ($a_3$), and a value describing the slope after the level for nonlinear behavior ($a_4$).

$$R = a_0 + \frac{a_1 * d^2}{a_2^2 + d^2},$$

where R is the mean discharge rate, and d is $$d = \left[ \frac{\left(a_3^{\left(\frac{1}{a_4}-1\right)}\right) * p^{\frac{1}{a_4}}}{\left(a_3^{\left(\frac{1}{a_4}-1\right)}\right) + p^{\left(\frac{1}{a_4}-1\right)}} \right]^{a_4}$$

where the variables denote the following:
$a_0$=the spontaneous discharge rate of the primary afferent,
$a_1$=the maximum increase of the discharge rate,
$a_2$=the sound pressure of the half maximum discharge rate,
$a_3$=the sound pressure at which nonlinear behavior occurs,
$a_4$=the exponent of the power-law slope in the nonlinear region, p the sound pressure level at the tympanic membrane, and
p=10*log 10(abs(S1(frequency,:))), where S1 is the Short Time Fourier Transform (STFT) of the acoustic signal.

Figure 8C:
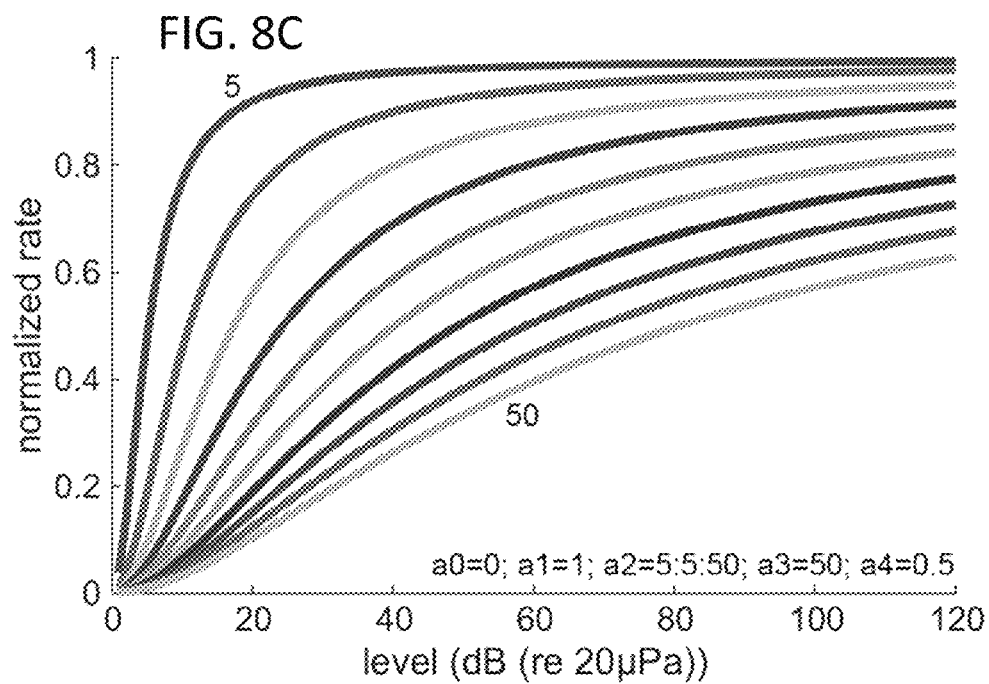
Figure 8D:
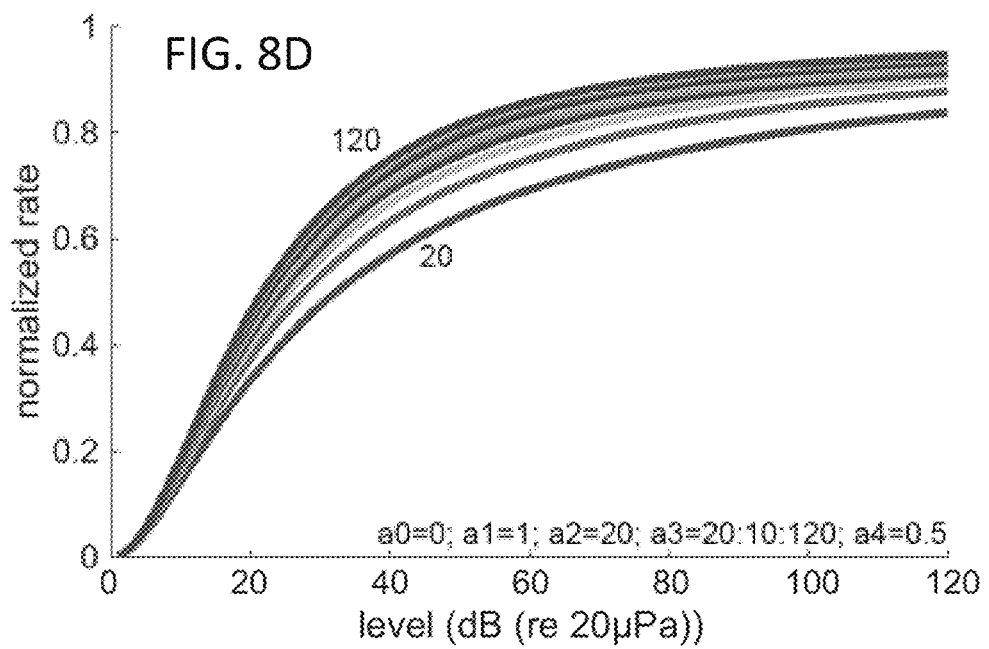
Figure 9:
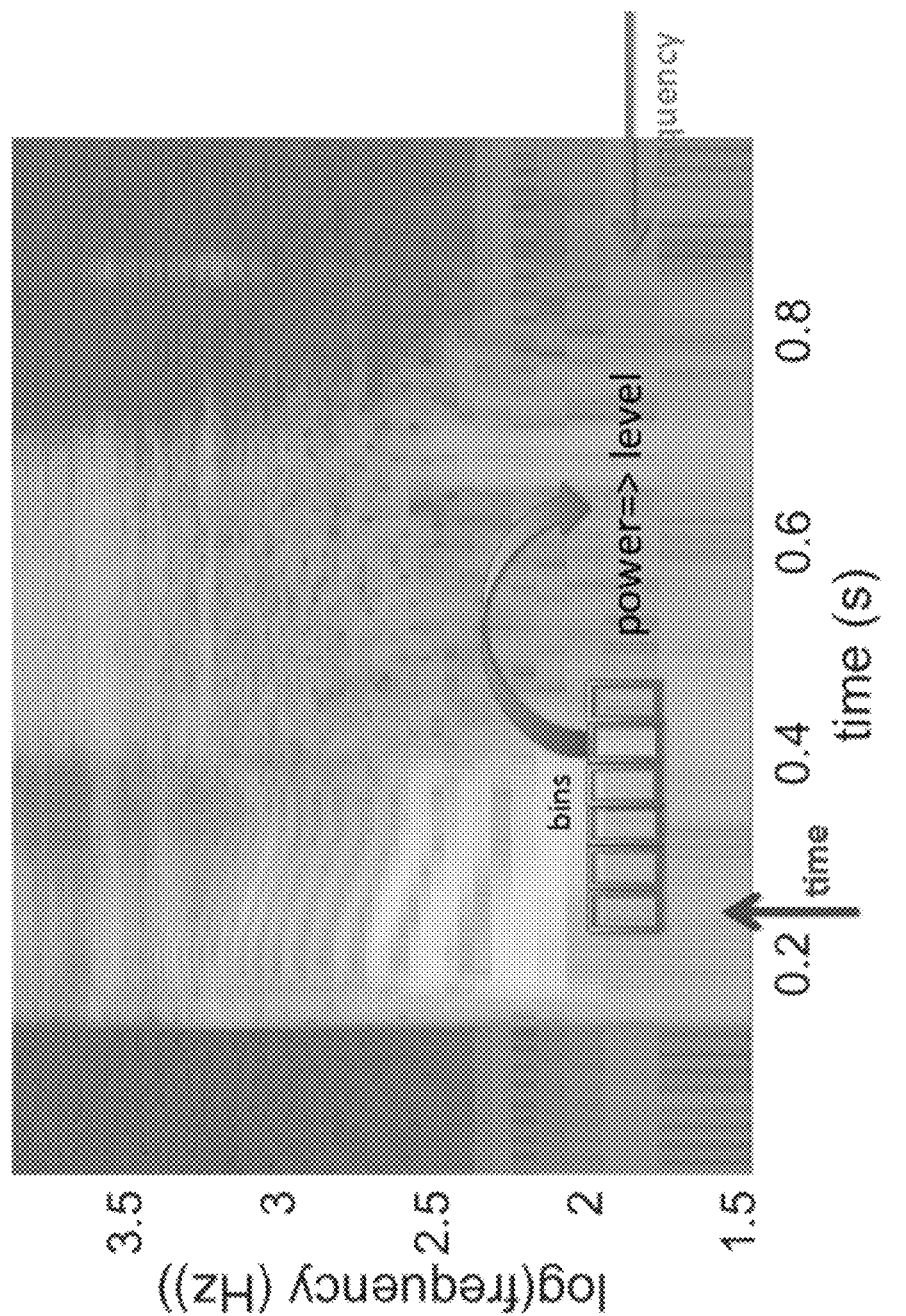
FIG. 9 shows a method to calculate the normalized level from the spectrogram. according to one embodiment of the present invention. The calculation of the normalized rate results in nonlinearly mapping the power of the acoustic signal.

Traces in FIG. 8A show that the spontaneous discharge rate $a_0$ shifts the curve towards larger values. The maximum rate $a_1$ limits the maximum rate to the number selected (FIG. 8B). The level for threshold $a_2$ has large effects on the mapping. Low threshold values result in a fast increase in the rate and quick saturation whereas large threshold values slow the increase in rate but limit the maximum in achievable rate (FIG. 8C). Smaller effects are seen from the parameters $a_3$ and $a_4$ (FIGS. 8D and 8E). Default values are selected ($a_0$=0, $a_1$=1; $a_2$=20; $a_3$=50, and $a_4$=0.5), which must be adjusted individually during later sessions with the CI user. For the calculation of the normalized rate, which is called PowerProb, a level is calculated from each bin along a row in the spectrogram, as shown in FIG. 9. The calculation of the normalized rate results in nonlinearly mapping the power of the acoustic signal.

Simple Phase Correction:

An acoustic signal can be decomposed into an envelope and fine structure. Part of the fine structure is the phase information of the signal. It has been pointed out that the phase information is crucial in processing acoustic information, in particular in challenging listening environments. In the normal hearing auditory system, it has been shown that phase is encoded on the auditory nerve by the timed occurrence of action potentials (phase locking). In other words, after a neuron generated an action potential, the probability for another action potential has a maximum at integer numbers of cycles following the last action potential. According to the invention the coding has been developed similarly. In its simplest version, at the occurrence of an electrical pulse, PhaseProb is set to 0 and increases linearly to 1 over the time of 1/(center frequency) of the selected frequency band in the spectrogram. At each integer number of cycle times, PhaseProb is reset to 0. The ramplike increase in probability can also be replaced by a Gaussian distribution of the probability with a maximum at the occurrence of a spike and the time between the maxima of 1/center frequency of the channel.

Advanced Phase Consideration:

Recent experiments have confirmed the importance of phase information. Recent tests with human subjects showed that distorting the phase and maintaining the correct magnitude information can render an intelligible signal unintelligible [105]. The latter experiments clearly emphasize the importance of phase information for speech recognition. In another series of experiments, pure tones, combinations of tones, filtered speech, and complex speech signals were played to the ear of anaesthetized guinea pigs. At the same time, the neural responses were recorded from the inferior colliculus. The results show that, independent of the best frequency of the neurons, the base frequency $f_0$ and the first formants $f_1$, and $f_2$ lead to phase-locked responses. In addition to those frequencies, which are typically well below 1 kHz, phase lock also occurs with the distortion products that can be calculated from the fundamental frequencies. Depending on location, distortion products above 0.5 kHz are boosted. Since CI users are typically not able to phase lock well above 0.5 kHz, the phase information of the distortion products has not been tested with this version of the code.

Amplitude Adjustment of Electrical Pulses (Optional):

Each bin of the spectrogram, which was calculated from the acoustical signal, represents the power in a given frequency band over a 3-12 ms time interval. The length of the time interval depends on the selection of points used to calculate the Short Time Fourier Transform (STFT). The power obtained through the spectrogram can then be used to adjust the amplitude of the train of electrical pulses. As described above in the section of intensity mapping and normalized rate—calculation of PowerProb, the power is mapped from the spectrogram and PowerProb is calculated. PowerProb is a number of [0,1] and can be assigned a weighing factor $w_{power}$. Analysis of the timing from the patterns seen in the pulse table shows that fine structure is encoded as seen in the neural responses in the ICC (FIGS. 8A-8E).

In another aspect, the invention also relates to a cochlear implant providing frequency-modulated electrical pulse train. In some embodiments, the cochlear implant includes a plurality of electrodes; and a processor in communication with the plurality of electrodes. The processor is adapted for generating frequency-modulated electrical pulse trains in one or more of the plurality of electrodes in response to operations of dividing data representing audio spanning a plurality of frequency bands into a plurality of bins associated with each of the frequency bands, each bin representing an energy level of the audio data within the frequency band within a period of time; associating each frequency band with a phase probability that starts at an initial phase probability value, resets to a minimum phase probability value after a pulse is generated, and increases from the minimum phase probability value to a maximum phase probability value over a period of time; for each bin, assigning a power probability as a normalized intensity for each bin, the normalized intensity being a number between a minimum power probability and a maximum power probability representing the energy level of the bin; and for each bin, generating a pulse in an electrode associated with the frequency band associated with the bin when a random number generated is less than the power probability divided by the phase probability. In certain embodiments, the number of frequency bands corresponds to the number of electrodes in the cochlear implant. The period of time is equal to one divided by the center frequency of the frequency band.

In certain embodiments, a pulse rate in the electrode associated with the frequency band associated with the bin varies between zero pulses per second and a maximum pulses per second.

In certain embodiments, the initial phase probability value is equal to the maximum phase probability value.

In certain embodiments, the phase probability increases linearly, or increases according to a Gaussian function.

In certain embodiments, the random number generated is a random number between a minimum modified power probability and a maximum modified power probability; the minimum modified power probability defined as a smallest possible value of the power probability divided by the phase probability and the maximum modified power probability defined as a largest possible value of the power probability divided by the phase probability.

It should be noted that all or a part of the steps or operations of the FMPC according to the embodiments of the present invention is implemented by hardware such as a cochlear implant or a program instructing relevant hardware. Yet another aspect of the invention provides a non-transitory computer-readable storage medium which stores computer executable instructions or program codes. When executed by one or more processors, the computer executable instructions or program codes enable a cochlear implant to complete various steps/operations in the above disclosed FMPC for generating frequency-modulated electrical pulse trains in the cochlear implant. The storage medium includes, but not limited to, a memory, or the likes.

IMPLEMENTATIONS AND EXAMPLES

Without intention to limit the scope of the invention, exemplary methods and their related results according to the embodiments of the present invention are given below.

Patient Population Tested:

the demographics of the patients tested are listed in a table shown in FIG. 10, where the digital numbers following a character "#" in the first column of the table are an identification of a participant. The participants are grouped based on the CI devices implanted. One group is for the participants having Med-El devices implanted and the other group is for the participants having Advanced Bionics devices implanted.

Sentence Recognition:

Sentence recognition was tested in all participants with sentences from the hearing in noise test (HINT, but with noise removed). Loudness was adjusted to "comfort level" by stepwise increasing the current amplitude at all of the active electrodes while a test sentence was played. The current level was increased until the patient ranked the loudness at "5" on a scale of 0 (not audible) to 10 (painful). No further adjustments of the map were made. A set of 10 sentences was played up to three times via the RIB2 research interface to the participant's cochlear implant. The participant was asked to repeat what he/she understood and to describe the listening experience. The number of correct words was counted. The score was calculated by dividing the number of correct words by the total number of words.

Figure 12:
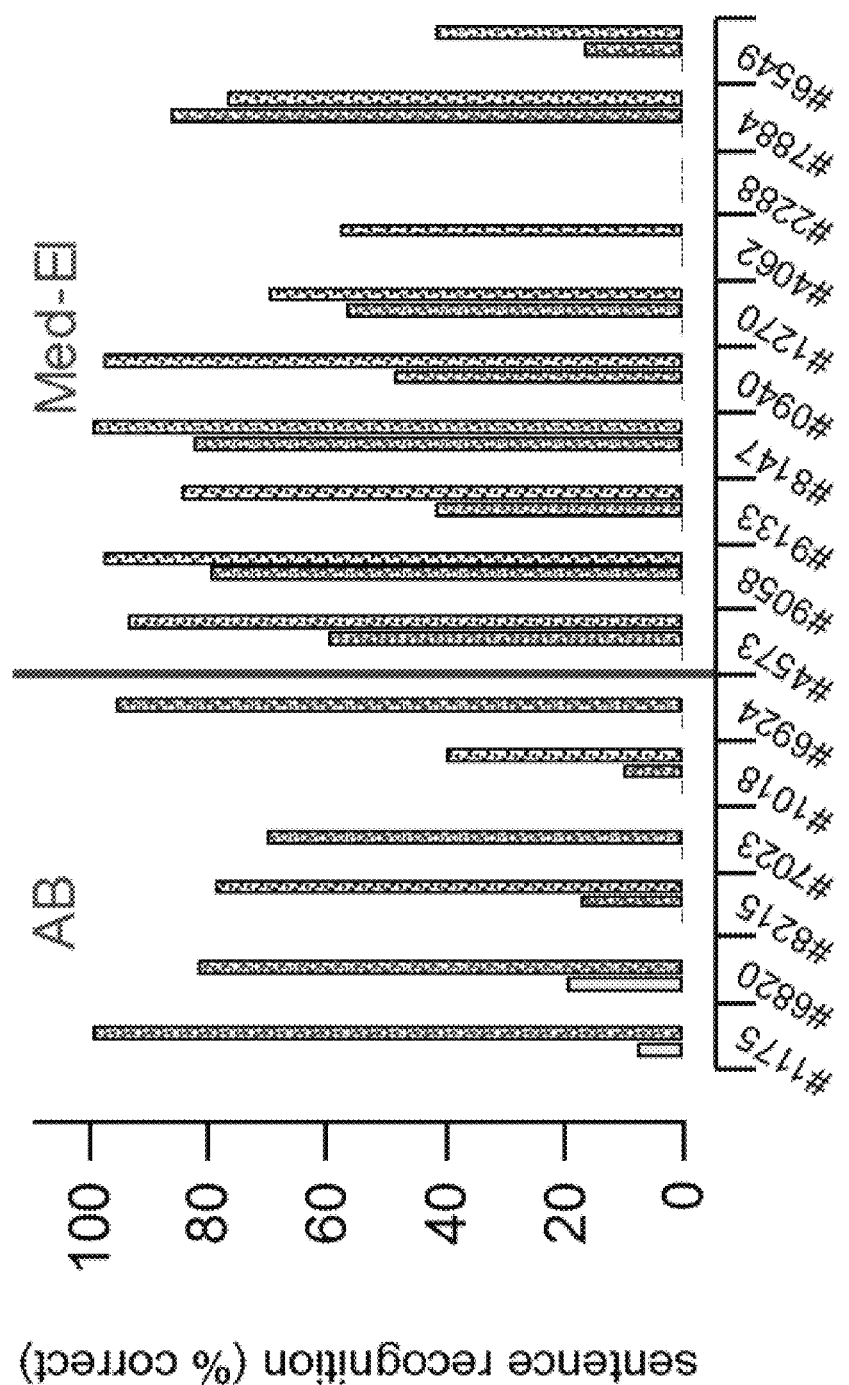
FIG. 12 shows individual results in sentence recognition. Each participant (# . . . ) has three performance parameters. Left bar: just after switching to the FMPC according to the present invention. Middle bar: after the read along. Right bar: with their device company's processor. Number of subjects is 10 with a Med-El implant and 6 with an AB implant.
Figure 13:
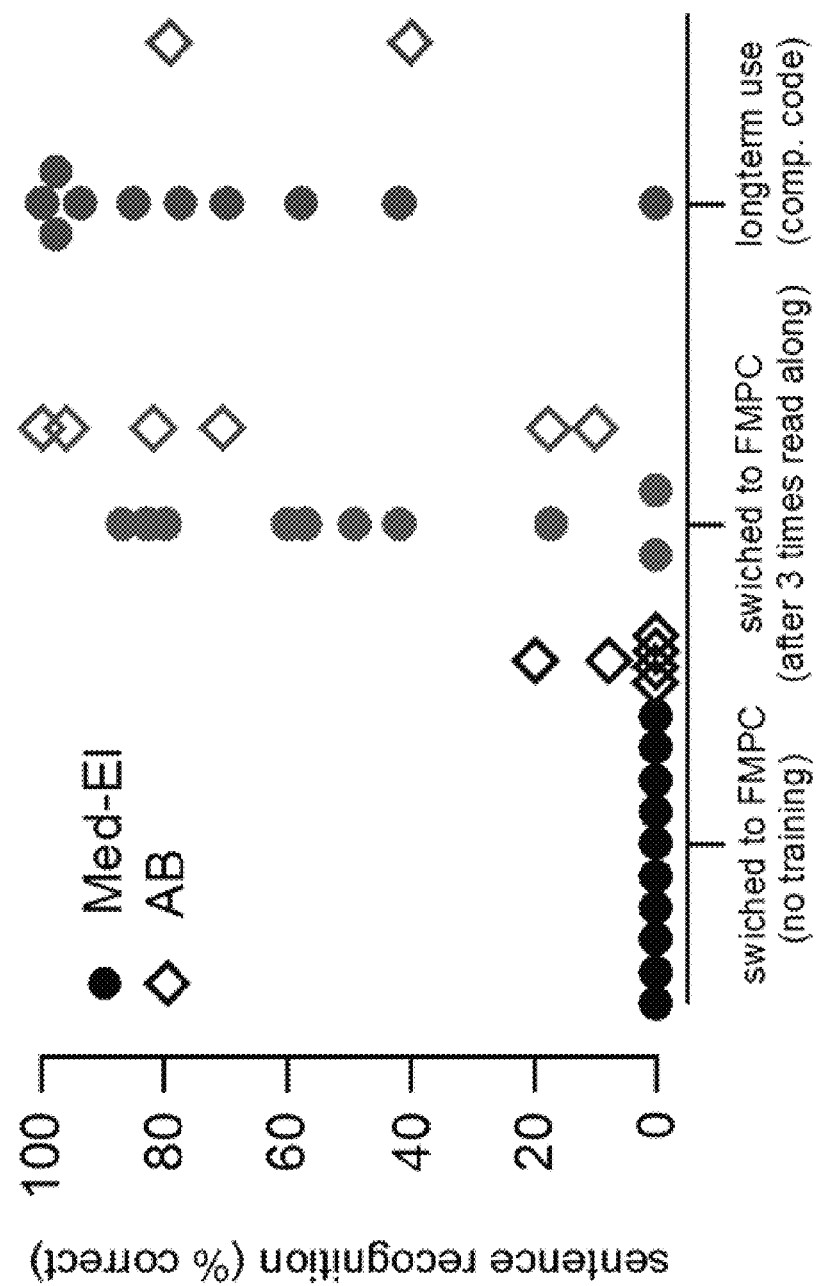
FIG. 13 shows combined results in sentence recognition. Left data set (black circles/diamonds) are the results just after switching to the FMPC according to the present invention. Almost no words could be recognized. Middle data set (green circles/diamonds) shows the scores after the read along exercise. Most of the subjects had word recognition above 40%. Right data set (red circles/diamonds) shows the results obtained with their Med-El/AB processor. Number of participants is 16, where 10 participants are with a Med-El processor, and 6 participants are with an AB processor.

Typically, the participants could not recognize sentences when played the first three times. Next, the participants were allowed to read along the set of sentences. This exercise was repeated in total not more than three times. After the read-along, the participants were asked again to repeat what he/she heard and to describe the listening experience. The set of sentences was repeated twice before new material was selected. Best performance is shown in FIGS. 11-13 and is compared with the performance of the individuals on the same material with their own processor and coding strategy (FIGS. 12 and 13). The data obtained in the individual sessions are shown in FIGS. 14A-14C.

When the performance with the invented novel code and the Med-El processor is directly compared, the scores with the invented novel code are on average 24.8 percent points lower than the scores obtained with the Med-El processing code. Note that the invented novel code has only been used for a short time. For the AB code the data are still not fully analyzed. However, it shows that 50% of the test subjects reached >80% in their speech recognition scores one 100% and one 96%.

Figure 15:
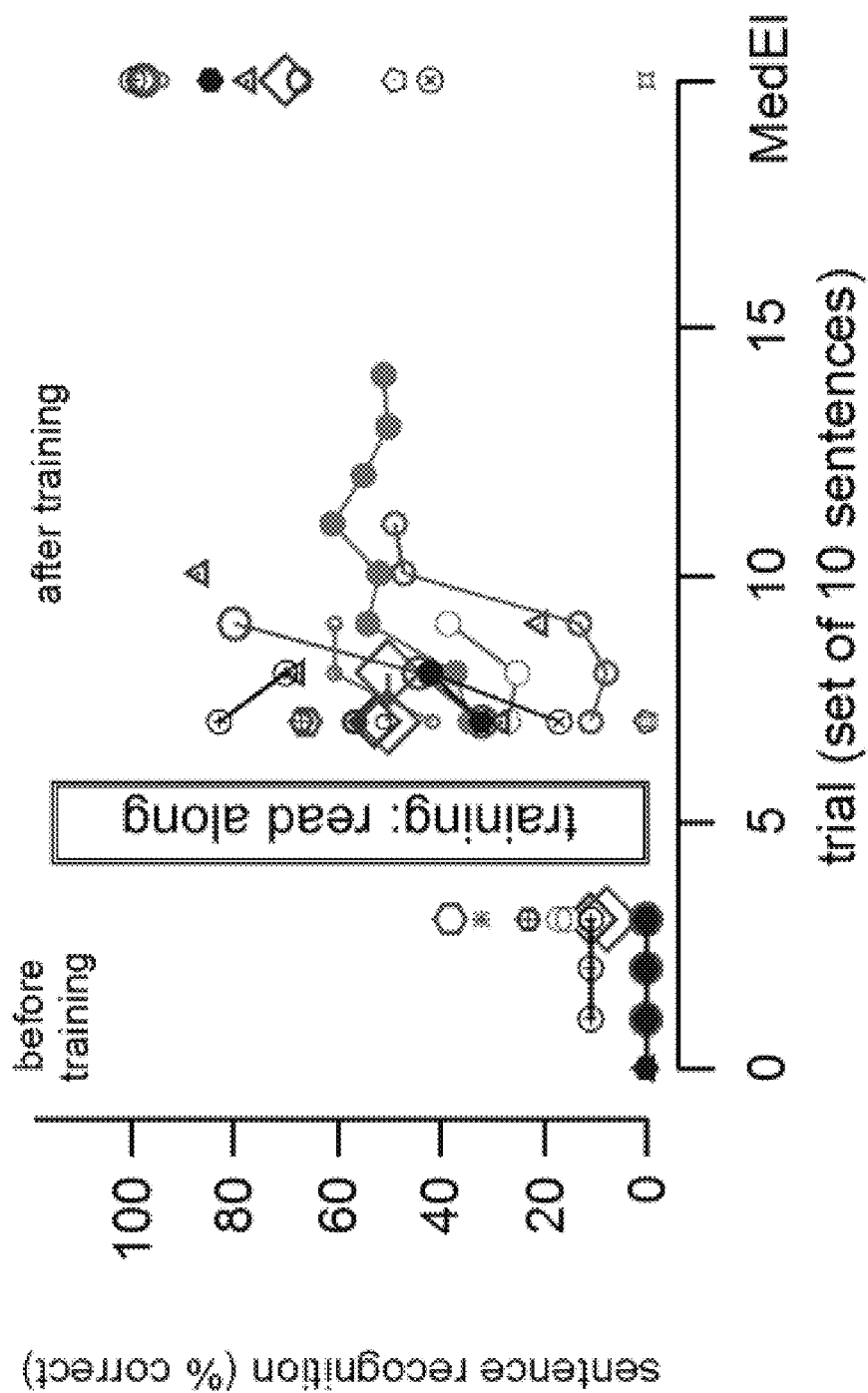
FIG. 15 shows scores obtained during the sentence recognition test according to embodiments of the present invention.
Figure 16:
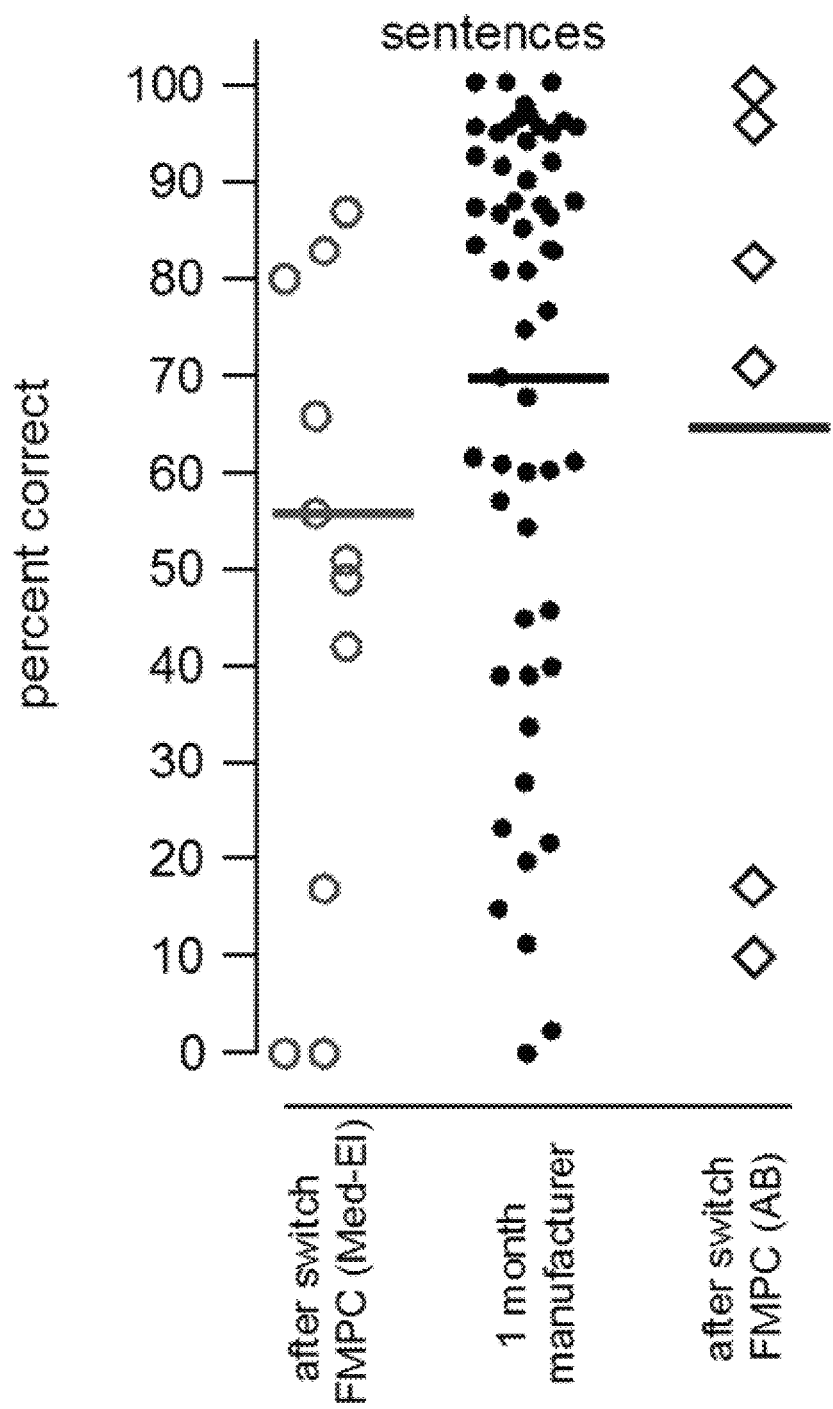
FIG. 16 shows scores obtained during the sentence test according to embodiments of the present invention. Scores are compared with published values.

Learning plays a role in performance. In the previous section it has been shown that switching from the Med-El processor to the invented novel code made a difference. First, the patient could not make out words. After reading along, the test subjects were able to perform with the new coding strategy. With an increasing number of repetitions, the test participants tended to improve steadily in their performance (FIG. 15). Note that each trial is one set of 10 sentences from the HINT. Typically, the performance for the patient is achieved after less than 20 sets of sentences or less than 200 sentences.

Figure 17:
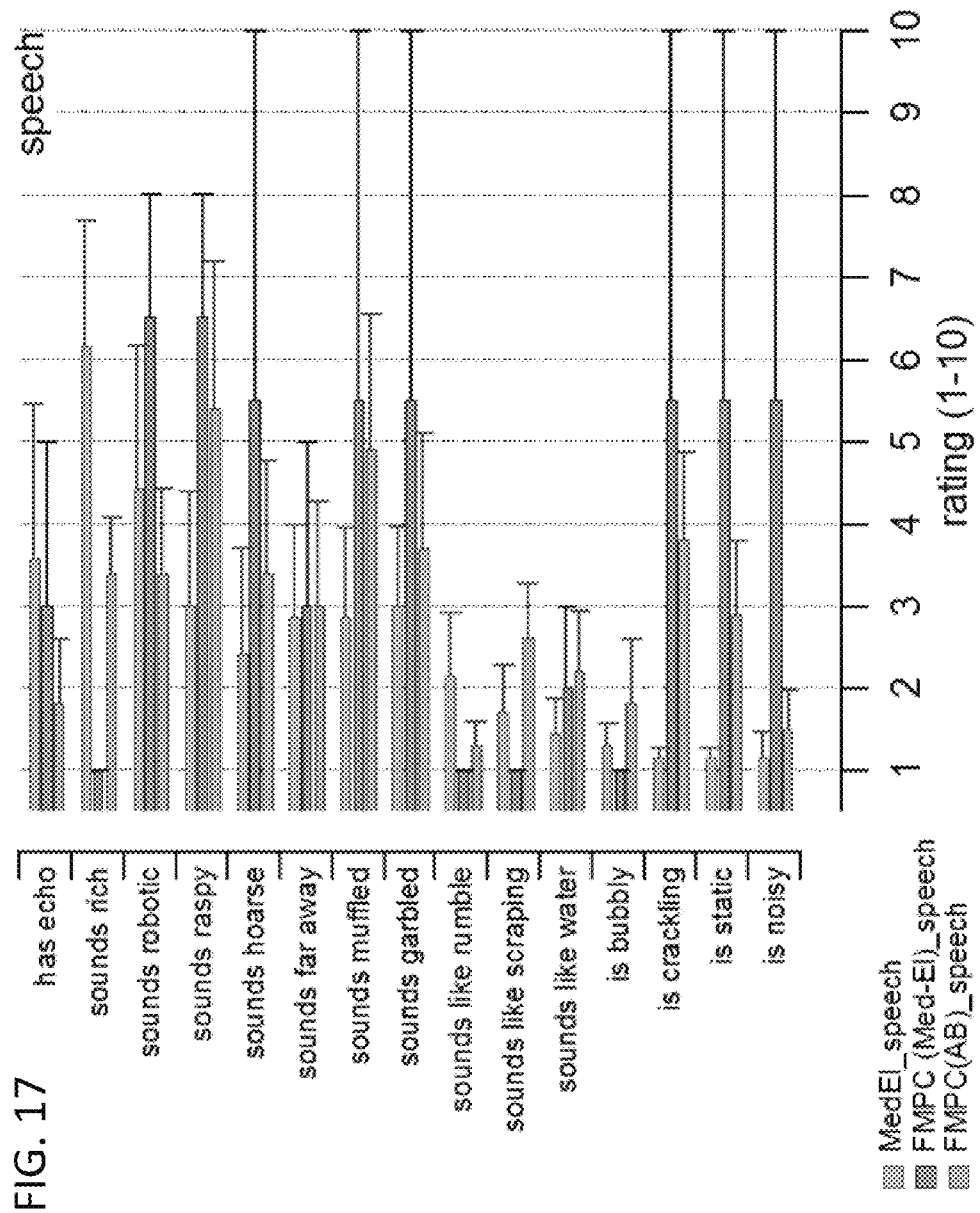
FIG. 17 shows patient ranking of listening experience to speech.
Figure 18:
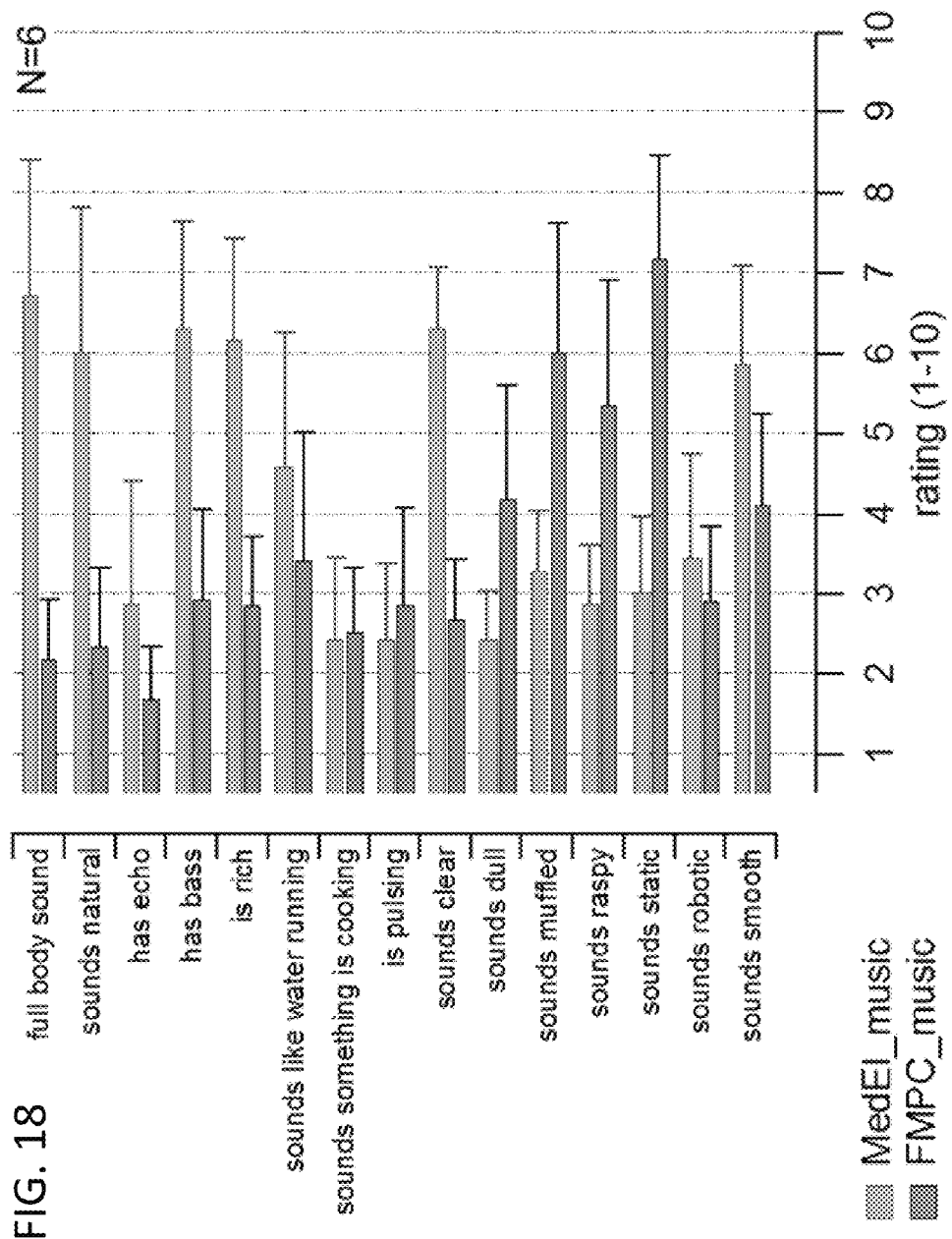
FIG. 18 shows patient ranking of listening experience to music.

Listening Experience:

Test participants were asked to describe their listening experience. During the initial test sessions, the participants expressed their hearing experience with the invented novel coding strategy and while using their own processor using their own words. The descriptors were collected and compiled into a list. A subset of 6 test subjects was then presented with the list of descriptors and the subjects were asked to rank them on a scale of 1 to 10. The results are obtained for speech (FIG. 17) and while listening to music (FIG. 18) for the participants with a cochlear implant from Med-El.

Figure 19A:
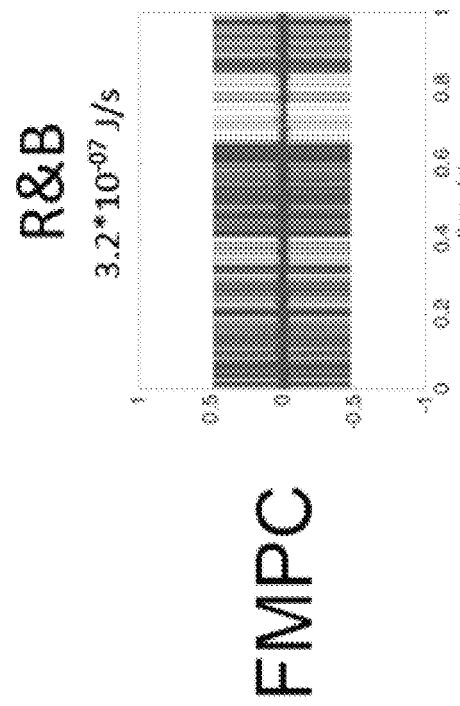
FIGS. 19A and 19B show a pulse pattern created with the novel code according to the present invention for rock music and R&B, respectively.
Figure 19B:
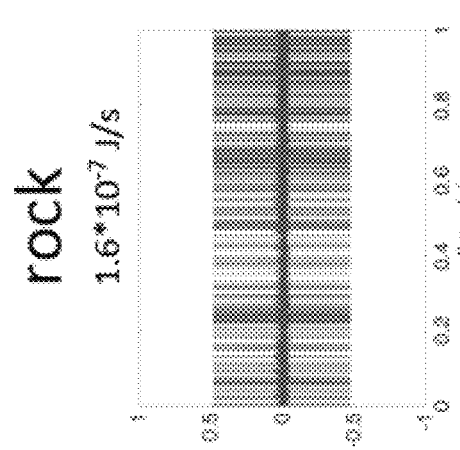
Figure 19C:
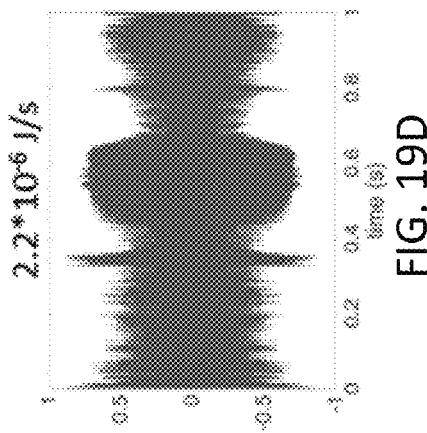
FIGS. 19C and 19D show the corresponding pulse pattern created for the same channel by a Med-El processor. Both stimulus paradigms are set for comfort loud. Significant power differences in total energy can be seen between the two coding strategies.
Figure 19D:
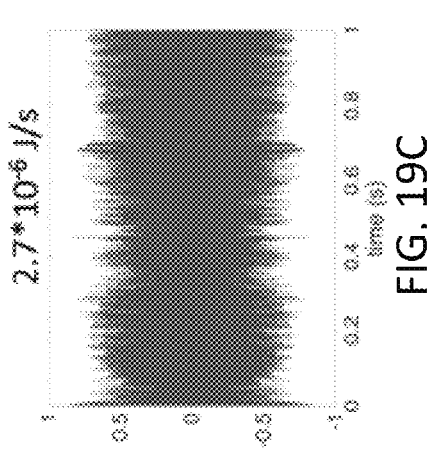

The results obtained for speech are shown in FIGS. 19A-19D, where FIGS. 19A and 19B shows the pulse pattern created with the invented novel code for rock music and R&B, respectively, and FIGS. 19C and 19D shows the corresponding pulse pattern created for the same channel by a Med-El processor for rock music and R&B, respectively. Both stimulus paradigms are set for comfort loud. Significant power differences in total energy can be seen between the two coding strategies Yes-No Questionnaire:

The results of questionnaire for the participants are listed in a table shown in FIG. 21. Note that not all songs contained every instrument.

Power Reduction:

The invented novel code encodes sound level by increasing pulse rate. A loudness growth between threshold for hearing and comfortably loud levels could be achieved in all of the participants. The settings that corresponded to a comfortably loud level were then used to visualize and record the pulse pattern at all of the electrodes. From the current amplitude and the pulse length, the corresponding total energy was calculated, which was delivered for each channel. The values for the invented novel code were compared to the values obtained from a Med-El processor. On average, the energy required for the invented novel code was 10 times less. Differences were more prominent for speech than for music. Typically for music the energy values for the novel code were about 3-8 times less. Typical examples for the electrodogram are shown in FIG. 19. The corresponding values are shown in the table in FIG. 20. Note that the Med-El processor was purchased from a user. Two electrodes were turned off and channel amplitudes were not at factory settings. For the FMPC, measurements were made using typical patient pulse tables.

Intensity limen and frequency limen are not tested.

Fixing the Phase:

For one test participant, the FMPC was changed such that the phase was fixed to zero. Fixing the phase rendered the information transmitted unintelligible. Even reading along with the text did not allow the test participant (#9058) to understand any word.

Fitting Procedure:

For two participants, an experimenter-controlled algorithm was tested to improve the fitting of the cochlear implant frequency map. Pairs of the same word were presented to the test subjects. The two versions of the word were generated with the FMPC with different frequency selections for the electrodes. The test participant had to listen to the pairs of words and decide which presentation was the more pleasant one. After a number of iterations, the algorithm converged to a "best solution". The resulting frequency map was then used to play speech and music. The test participants were asked to rank the changes on a scale of 1 to 10. The participants all found an improvement in sound quality. In two separate sessions, the test participant 1 ranked the improvement from 1 to 8 (#9058, first session), 1 to 8 (#9058, second session about 4 weeks after the first session). In the second session, the participant's speech performance was tested with new material (HINT3). The performance increased from 26.3% to 45.6% after fitting. The test participant 2 ranked the improvement from 4 to 5 (#4573). The speech performance remained the same after the fitting. Both test subjects describe the change in listening experience as having less background noise, less raspiness, and richer sound.

Platform has been developed for improved fitting. A demo-version exists for normal hearing subjects to determine robustness of the fitting and to demonstrate performance to an outsider.

Music Test:

For two subjects, the participants were tested on the CAMP musical timbre test; once with FMPC and once with their current processors. The preliminary results are shown in a table in FIG. 22.

As shown in the above exemplary results, according to the invention, about 10 times less electrical charge is delivered to the cochlea when compared to contemporary codes. Stimulation rate is dynamic and varies between 0 and 3600 pps. The average stimulation rate for speech is about 125 pps. Stimulation is allowed at all electrode contacts simultaneously. The invented novel code uses frequency modulation to encode intensity. Performance just after switching the code is below the performance after long-term use.

In the presently preferred embodiment of the invented novel code, the average pulse rate per channel ranges from about 27 to 69 pps encoding speech without noise and 91 to 358 pps encoding speech with noise. The pps for encoding music is comparable to encoding speech with noise, but with an average rate extending into the 400 pps range.

In the presently preferred embodiment, the channel rate ranges from 0 pps to the device maximum. With our current hardware limitations, the max is about 3,600 pps, but, ideally, the maximum rate should be as fast as a cochlear processor allows.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LIST OF REFERENCES

[1]. Shepherd, R. K. and N. A. Hardie, *Deafness-induced changes in the auditory pathway: implications for cochlear implants*. Audiology & neuro-otology, 2001. 6(6): p. 305-18.

[2]. Zeng, F. G., Q. Tang, and T. Lu, *Abnormal pitch perception produced by cochlear implant stimulation*. PloS one, 2014. 9(2): p. e88662.

[3]. Shepherd, R. K. and E. Javel, *Electrical stimulation of the auditory nerve. I. Correlation of physiological responses with cochlear status*. Hearing research, 1997. 108(1-2): p. 112-44.

[4]. Hartmann, R., G. Topp, and R. Klinke, *Discharge patterns of cat primary auditory fibers with electrical stimulation of the cochlea*. Hearing research, 1984. 13(1): p. 47-62.

[5]. van den Honert, C. and P. H. Stypulkowski, *Single fiber mapping of spatial excitation patterns in the electrically stimulated auditory nerve*. Hearing research, 1987. 29(2-3): p. 195-206.

[6]. van den Honert, C. and P. H. Stypulkowski, *Physiological properties of the electrically stimulated auditory nerve. II. Single fiber recordings*. Hearing research, 1984. 14(3): p. 225-43.

[7]. Tirko, N. N. and D. K. Ryugo, *Synaptic plasticity in the medial superior olive of hearing, deaf and cochlear-implanted cats*. The Journal of comparative neurology, 2012. 520(10): p. 2202-17.

[8]. Baker, C. A., et al., *Postnatal development of the endbulb of held in congenitally deaf cats*. Frontiers in neuroanatomy, 2010. 4: p. 19.

[9]. Ryugo, D. K., et al., *Separate forms of pathology in the cochlea of congenitally deaf white cats*. Hearing research, 2003. 181(1-2): p. 73-84.

[10]. Redd, E. E., et al., *The effects of congenital deafness on auditory nerve synapses: Type I and Type II multipolar cells in the anteroventral cochlear nucleus of cats*. Journal of the Association for Research in Otolaryngology: JARO, 2002. 3(4): p. 403-17.

[11]. Redd, E. E., T. Pongstaporn, and D. K. Ryugo, *The effects of congenital deafness on auditory nerve synapses and globular bushy cells in cats*. Hearing research, 2000. 147(1-2): p. 160-74.

[12]. Ryugo, D. K., et al., *Ultrastructural analysis of primary endings in deaf white cats: morphologic alterations in endbulbs of Held*. The Journal of comparative neurology, 1997. 385(2): p. 230-44.

[13]. Saada, A. A., J. K. Niparko, and D. K. Ryugo, *Morphological changes in the cochlear nucleus of congenitally deaf white cats*. Brain research, 1996. 736(1-2): p. 315-28.

[14]. Limb, C. J., et al., *Auditory cortical activity during cochlear implant-mediated perception of spoken language, melody, and rhythm*. Journal of the Association for Research in Otolaryngology: JARO, 2010. 11(1): p. 133-43.

[15]. Naito, Y., et al., *Increased cortical activation during hearing of speech in cochlear implant users*. Hearing research, 2000. 143(1-2): p. 139-46.

[16]. Wong, D., et al., *PET imaging of cochlear-implant and normal-hearing subjects listening to speech and non-speech*. Hearing research, 1999. 132(1-2): p. 34-42.

[17]. Gfeller, K., et al., *The effects of familiarity and complexity on appraisal of complex songs by cochlear implant recipients and normal hearing adults*. Journal of music therapy, 2003. 40(2): p. 78-112.

[18]. Stordahl, J., *Song recognition and appraisal: a comparison of children who use cochlear implants and normally hearing children*. Journal of music therapy, 2002. 39(1): p. 2-19.

[19]. Aggarwal, R. and K. M. Green, *Cochlear implants and positron emission tomography*. The Journal of laryngology and otology, 2012. 126(12): p. 1200-3.

[20]. Green, K. M., et al., *Cortical plasticity in the first year after cochlear implantation*. Cochlear implants international, 2008. 9(2): p. 103-17.

[21]. Coez, A., et al., *Cochlear implant benefits in deafness rehabilitation: PET study of temporal voice activations*. Journal of nuclear medicine: official publication, Society of Nuclear Medicine, 2008. 49(1): p. 60-7.

[22]. Naito, Y., et al., *Development and plasticity of the auditory cortex in cochlear implant users: a follow-up study by positron emission tomography*. Advances in otorhino-laryngology, 2000. 57: p. 55-9.

[23]. Miyamoto, R. T. and D. Wong, *Positron emission tomography in cochlear implant and auditory brainstem implant recipients*. Journal of communication disorders, 2001. 34(6): p. 473-8.

[24]. Hirano, S., et al., *Functional differentiation of the auditory association area in prelingually deaf subjects*. Auris, nasus, larynx, 2000. 27(4): p. 303-10.

[25]. Truy, E., et al., *Auditory cortex activity changes in long-term sensorineural deprivation during crude cochlear electrical stimulation: evaluation by positron emission tomography*. Hearing research, 1995. 86(1-2): p. 34-42.

[26]. Shannon, R. V., Q. J. Fu, and J. Galvin, 3rd, *The number of spectral channels required for speech recognition depends on the difficulty of the listening situation*. Acta oto-laryngologica. Supplementum, 2004(552): p. 50-4.

[27]. Fishman, K. E., R. V. Shannon, and W. H. Slattery, *Speech recognition as a function of the number of electrodes used in the SPEAK cochlear implant speech processor*. Journal of speech, language, and hearing research: JSLHR, 1997. 40(5): p. 1201-15.

[28]. Reiss, L. A., et al., *Consonant recognition as a function of the number of stimulation channels in the Hybrid short-electrode cochlear implant*. The Journal of the Acoustical Society of America, 2012. 132(5): p. 3406-17.

[29]. Snel-Bongers, J., et al., *Spread of excitation and channel interaction in single-and dual-electrode cochlear implant stimulation*. Ear and hearing, 2012. 33(3): p. 367-76.

[30]. Dorman, M., et al., *Consonant recognition as a function of the number of channels of stimulation by patients who use the Symbion cochlear implant.* Ear and hearing, 1989. 10(5): p. 288-91.
[31]. Shannon, R. V., *Multichannel electrical stimulation of the auditory nerve in man. II. Channel interaction.* Hearing research, 1983. 12(1): p. 1-16.
[32]. Shannon, R. V., *Multichannel electrical stimulation of the auditory nerve in man. I. Basic psychophysics.* Hearing research, 1983. 11(2): p. 157-89.
[33]. Kral, A., et al., *Spatial resolution of cochlear implants: the electrical field and excitation of auditory afferents.* Hearing research, 1998. 121(1-2): p. 11-28.
[34]. Liang, D. H., H. S. Lusted, and R. L. White, *The nerve-electrode interface of the cochlear implant: current spread.* IEEE transactions on bio-medical engineering, 1999. 46(1): p. 35-43.
[35]. Black, R. C., et al., *Current distributions in cochlear stimulation.* Annals of the New York Academy of Sciences, 1983. 405: p. 137-45.
[36]. Micco, A. G. and C. P. Richter, *Tissue resistivities determine the current flow in the cochlea.* Current opinion in otolaryngology & head and neck surgery, 2006. 14(5): p. 352-5.
[37]. Micco, A. G. and C. P. Richter, *Electrical resistivity measurements in the mammalian cochlea after neural degeneration.* The Laryngoscope, 2006. 116(8): p. 1334-41.
[38]. Firszt, J. B., et al., *Current steering creates additional pitch percepts in adult cochlear implant recipients.* Otology & neurotology: official publication of the American Otological Society, American Neurotology Society [and] European Academy of Otology and Neurotology, 2007. 28(5): p. 629-36.
[39]. Baskent, D. and R. V. Shannon, *Interactions between cochlear implant electrode insertion depth and frequency-place mapping.* The Journal of the Acoustical Society of America, 2005. 117(3 Pt 1): p. 1405-16.
[40]. Nelson, D. A., et al., *Intensity discrimination as a function of stimulus level with electric stimulation.* The Journal of the Acoustical Society of America, 1996. 100(4 Pt 1): p. 2393-414.
[41]. Smith, Z. M., B. Delgutte, and A. J. Oxenham, *Chimaeric sounds reveal dichotomies in auditory perception.* Nature, 2002. 416(6876): p. 87-90.
[42]. Voelcker, H. B., *Toward a unified theory of modulation.* Proceedings of the IEEE, 1966. 54(3): p. 340.
[43]. Rice, S. O., *Distortion produced by band limitation of an FM wave.* The Bell System Technical Journal, 1973. 52(5): p. 605-626.
[44]. Logan, B. F. J., *Information in the zero crossings of bandpass signals.* The Bell System Technical Journal, 1977. 56(4): p. 487-510.
[45]. Sachs, M. B., *Neural coding of complex sounds: speech.* Annu Rev Physiol, 1984. 46: p. 261-73.
[46]. Whiteford, K. L. and A. J. Oxenham, *Using individual differences to test the role of temporal and place cues in coding frequency modulation.* J Acoust Soc Am, 2015. 138(5): p. 3093.
[47]. Javel, E. and J. B. Mott, *Physiological and psychophysical correlates of temporal processes in hearing.* Hear Res, 1988. 34(3): p. 275-94.
[48]. Rutherford, W., *A New Theory of Hearing.* J Anat Physiol, 1886. 21 (Pt 1): p. 166-8.
[49]. Wever, E. G. and C. W. Bray, *Action Currents in the Auditory Nerve in Response to Acoustical Stimulation.* Proc Natl Acad Sci USA, 1930. 16(5): p. 344-50.
[50]. Wever, E. G. and C. W. Bray, *Auditory Nerve Impulses.* Science, 1930. 71(1834): p. 215.
[51]. Johnson, D. H., *The relationship between spike rate and synchrony in responses of auditory-nerve fibers to single tones.* J Acoust Soc Am, 1980. 68(4): p. 1115-22.
[52]. Joris, P. X. and T. C. Yin, *Responses to amplitude-modulated tones in the auditory nerve of the cat.* J Acoust Soc Am, 1992. 91(1): p. 215-32.
[53]. Tasaki, I., *Nerve impulses in individual auditory nerve fibers of guinea pig.* J Neurophysiol, 1954. 17(2): p. 97-122.
[54]. Kiang, N. Y., et al., *Discharge pattern of single fibers in cat's auditory nerve.*, N. Y. Kiang, et al., Editors. 1965, MIT Press: Cambridge, Mass.
[55]. Rose, J. E., et al., *Phase-locked response to low-frequency tones in single auditory nerve fibers of the squirrel monkey.* J Neurophysiol, 1967. 30(4): p. 769-93.
[56]. Rupert, A., G. Moushegian, and R. Galambos, *Unit responses to sound from auditory nerve of the cat.* J Neurophysiol, 1963. 26: p. 449-65.
[57]. Oxenham, A. J., *Revisiting place and temporal theories of pitch.* Acoust Sci Technol, 2013. 34(6): p. 388-396.
[58]. Drullman, R., *Temporal envelope and fine structure cues for speech intelligibility.* J Acoust Soc Am, 1995. 97(1): p. 585-92.
[59]. Shannon, R. V., et al., *Speech recognition with primarily temporal cues.* Science, 1995. 270(5234): p. 303-4.
[60]. Moon, I. J. and S. H. Hong, *What is temporal fine structure and why is it important?* Korean J Audiol, 2014. 18(1): p. 1-7.
[61]. Shamma, S. and C. Lorenzi, *On the balance of envelope and temporal fine structure in the encoding of speech in the early auditory system.* J Acoust Soc Am, 2013. 133(5): p. 2818-33.
[62]. Wilson, B. S., *Getting a decent (but sparse) signal to the brain for users of cochlear implants.* Hear Res, 2015. 322: p. 24-38.
[63]. Hill, F. J., L. P. McRae, and R. P. McClellan, *Speech recognition as a function of channel capacity in a discrete set of channels.* J Acoust Soc Am, 1968. 44(1): p. 13-8.
[64]. Shannon, R. V., et al., *Speech perception with cochlear implants.*, in *Cochlear implants: Auditory protheses and electric hearing.*, F.-G. Zheng, A. N. Popper, and R. R. Fay, Editors. 2006, Springer: New York. p. 334-376.
[65]. Gnansia, D., et al., *Effects of spectral smearing and temporal fine structure degradation on speech masking release.* J Acoust Soc Am, 2009. 125(6): p. 4023-33.
[66]. Hopkins, K. and B. C. Moore, *The contribution of temporal fine structure to the intelligibility of speech in steady and modulated noise.* J Acoust Soc Am, 2009. 125(1): p. 442-6.
[67]. Swaminathan, J. and M. G. Heinz, *Psychophysiological analyses demonstrate the importance of neural envelope coding for speech perception in noise.* J Neurosci, 2012. 32(5): p. 1747-56.
[68]. Qin, M. K. and A. J. Oxenham, *Effects of simulated cochlear-implant processing on speech reception in fluctuating maskers.* J Acoust Soc Am, 2003. 114(1): p. 446-54.
[69]. Nie, K., G. Stickney, and F. G. Zeng, *Encoding frequency modulation to improve cochlear implant performance in noise.* IEEE Trans Biomed Eng, 2005. 52(1): p. 64-73.

[70]. Dillier, N., et al., *Encoding and decoding of auditory signals in relation to human speech and its application to human cochlear implants.* Audiology, 1980. 19(2): p. 146-63.

[71]. Wilson, B. S., et al., *Better speech recognition with cochlear implants.* Nature, 1991. 352(6332): p. 236-8.

[72]. Koch, D. B., et al., *Using current steering to increase spectral resolution in CII and HiRes 90K users.* Ear Hear, 2007. 28(2 Suppl): p. 38S-41S.

[73]. Firszt, J. B., et al., *Current steering creates additional pitch percepts in adult cochlear implant recipients.* Otol Neurotol, 2007. 28(5): p. 629-36.

[74]. Spahr, A. J., et al., *Simulating the effects of spread of electric excitation on musical tuning and melody identification with a cochlear implant.* J Speech Lang Hear Res, 2008. 51(6): p. 1599-606.

[75]. Bonham, B. H. and L. M. Litvak, *Current focusing and steering: modeling, physiology, and psychophysics.* Hear Res, 2008. 242(1-2): p. 141-53.

[76]. Hu, Y. and P. C. Loizou, *A new sound coding strategy for suppressing noise in cochlear implants.* J Acoust Soc Am, 2008. 124(1): p. 498-509.

[77]. Buechner, A., et al., *A high rate n-of-m speech processing strategy for the first generation Clarion cochlear implant.* Int J Audiol, 2009. 48(12): p. 868-75.

[78]. Tyler, R. S., et al., *Evaluation of different choices of n in an n of m processor for cochlear implants.* Adv Otorhinolaryngol, 2000. 57: p. 311-5.

[79]. Stickney, G. S., K. Nie, and F. G. Zeng, *Contribution of frequency modulation to speech recognition in noise.* J Acoust Soc Am, 2005. 118(4): p. 2412-20.

[80]. Zeng, F. G., et al., *Speech recognition with amplitude and frequency modulations.* Proc Natl Acad Sci USA, 2005. 102(7): p. 2293-8.

[81]. Wilson, B. S., et al., *Coding strategies for multichannel cochlear prostheses.* Am J Otol, 1991. 12 Suppl: p. 56-61.

[82]. Faltys, M. A., et al., *Multichannel cochlear prosthesis with flexible control of stimulus waveforms.* 2001, Google Patents.

[83]. Melo, T. M., M. C. Bevilacqua, and O. A. Costa, *Speech perception in cochlear implant users with the HiRes 120 strategy: a systematic review.* Braz J Otorhinolaryngol, 2012. 78(3): p. 129-33.

[84]. Chang, Y. T., et al., *Tone discrimination and speech perception benefit in Mandarin-speaking children fit with HiRes fidelity 120 sound processing.* Otol Neurotol, 2009. 30(6): p. 750-7.

[85]. Firszt, J. B., et al., *Speech recognition in cochlear implant recipients: comparison of standard HiRes and HiRes 120 sound processing.* Otol Neurotol, 2009. 30(2): p. 146-52.

[86]. Han, D., et al., *Lexical tone perception with HiResolution and HiResolution 120 sound-processing strategies in pediatric Mandarin-speaking cochlear implant users.* Ear Hear, 2009. 30(2): p. 169-77.

[87]. Kos, M. I., et al., *Immuno-detection of Staphylococcus aureus biofilm on a cochlear implant.* Infection, 2009. 37(5): p. 450-4.

[88]. Landsberger, D. M. and A. G. Srinivasan, *Virtual channel discrimination is improved by current focusing in cochlear implant recipients.* Hear Res, 2009. 254(1-2): p. 34-41.

[89]. Park, H. J., et al., *HiRes with Fidelity 120 benefit in native speakers of Korean.* Cochlear Implants Int, 2009. 10 Suppl 1: p. 85-8.

[90]. Runge-Samuelson, C. L., *Effects of high-rate pulse trains on electrode discrimination in cochlear implant users.* Trends Amplif, 2009. 13(2): p. 76-86.

[91]. Donaldson, G. S., P. K. Dawson, and L. Z. Borden, *Within-subjects comparison of the HiRes and Fidelity 120 speech processing strategies: speech perception and its relation to place-pitch sensitivity.* Ear Hear, 2011. 32(2): p. 238-50.

[92]. Kam, A. C., et al., *Evaluation of the ClearVoice Strategy in Adults Using HiResolution Fidelity 120 Sound Processing.* Clin Exp Otorhinolaryngol, 2012. 5 Suppl 1: p. S89-92.

[93]. Greenwood, D. D., *A cochlear frequency-position function for several species—29 years later.* The Journal of the Acoustical Society of America, 1990. 87(6): p. 2592-2605.

[94]. Nogueira, W., et al., *Design and evaluation of a cochlear implant strategy based on a "Phantom" channel.* PLoS One, 2015. 10(3): p. e0120148.

[95]. Fridman, G. Y., *Methods and apparatus for cochlear implant signal processing.* 2011, Google Patents.

[96]. Voelkel, A. W., *Stimulation channel selection methods.* 2010, Google Patents.

[97]. Nobbe, A., et al., *Frequency discrimination with sequential or simultaneous stimulation in MED-EL cochlear implants.* Acta oto-laryngologica, 2007. 127 (12): p. 1266-1272.

[98]. Zierhofer, C. M., *Electrical nerve stimulation based on channel specific sampling sequences.* 2003, Google Patents.

[99]. Neal, T. and B. van Dijk, *Determining stimulation signals for neural stimulation.* 2015, Google Patents.

[100]. James, C. J., *Stimulation channel selection for a stimulating medical device.* 2012, Google Patents.

[101]. Vandali, A. and G. M. Clark, *Emphasis of short-duration transient speech features.* 2008, Google Patents.

[102]. McDermott, H. J. and A. E. Vandali, *Spectral maxima sound processor.* 1997, Google Patents.

[103]. Killian, M., E. Von Wallenberg, and G. Smoorenburg, *Pulse burst electrical stimulation of nerve or tissue fibers.* 2008, Google Patents.

[104]. Wolfe, J. and E. Schafer, *Programming cochlear implants.* 2014: Plural Publishing.

[105]. Chen, F. and Y.-H. Lai, *Modeling speech intelligibility with recovered envelope from temporal fine structure stimulus.* Speech Communication, 2016. 81: p. 120-128.

[106]. Zeng, F. G., et al., *On the dichotomy in auditory perception between temporal envelope and fine structure cues.* J Acoust Soc Am, 2004. 116(3): p. 1351-4.

[107]. Rose, J. E., et al., *Some effects of stimulus intensity on response of auditory nerve fibers in the squirrel monkey.* J Neurophysiol, 1971. 34(4): p. 685-99.

[108]. Anderson, D. J., et al., *Temporal position of discharges in single auditory nerve fibers within the cycle of a sine-wave stimulus: frequency and intensity effects.* J Acoust Soc Am, 1971. 49(4): p. Suppl 2:1131+.

[109]. Brugge, J. F., et al., *Time structure of discharges in single auditory nerve fibers of the squirrel monkey in response to complex periodic sounds.* J Neurophysiol, 1969. 32(3): p. 386-401.

[110]. Kiang, N. Y., E. C. Moxon, and R. A. Levine, *Auditory-nerve activity in cats with normal and abnormal cochleas. In: Sensorineural hearing loss.* Ciba Found Symp, 1970: p. 241-73.

[111]. Kiang, N. Y., et al., *Stimulus coding in the cat's auditory nerve. Preliminary report.* Ann Otol Rhinol Laryngol, 1962. 71: p. 1009-26.

[112]. Liberman, M. C., *Single-neuron labeling in the cat auditory nerve*. Science, 1982. 216(4551): p. 1239-41.

[113]. Tasaki, I., *Nerve impulses in individual auditory nerve fibers in guinea pig*. J. Neurophysiol., 1954(17): p. 97-122.

[114]. Winter, P. and H. H. Funkenstein, *The effect of species-specific vocalization on the discharge of auditory cortical cells in the awake squirrel monkey. (Saimiri sciureus)*. Exp Brain Res, 1973. 18(5): p. 489-504.

[115]. Newman, J. D. and Z. Wollberg, *Responses of single neurons in the auditory cortex of squirrel monkeys to variants of a single call type*. Exp Neurol, 1973. 40(3): p. 821-4.

[116]. Newman, J. D. and Z. Wollberg, *Multiple coding of species-specific vocalizations in the auditory cortex of squirrel monkeys*. Brain Res, 1973. 54: p. 287-304.

[117]. Delgutte, B., *Speech coding in the auditory nerve: II. Processing schemes for vowel-like sounds*. J Acoust Soc Am, 1984. 75(3): p. 879-86.

[118]. Delgutte, B. and N. Y. Kiang, *Speech coding in the auditory nerve: V. Vowels in background noise*. J Acoust Soc Am, 1984. 75(3): p. 908-18.

[119]. Delgutte, B. and N. Y. Kiang, *Speech coding in the auditory nerve: IV. Sounds with consonant-like dynamic characteristics*. J Acoust Soc Am, 1984. 75(3): p. 897-907.

[120]. Delgutte, B. and N. Y. Kiang, *Speech coding in the auditory nerve: III. Voiceless fricative consonants*. J Acoust Soc Am, 1984. 75(3): p. 887-96.

[121]. Delgutte, B. and N. Y. Kiang, *Speech coding in the auditory nerve: I. Vowel-like sounds*. J Acoust Soc Am, 1984. 75(3): p. 866-78.

[122]. Miller, R. L., B. M. Calhoun, and E. D. Young, *Discriminability of vowel representations in cat auditory-nerve fibers after acoustic trauma*. J Acoust Soc Am, 1999. 105(1): p. 311-25.

[123]. Richter, C. P., S. Heynert, and R. Klinke, *Rate-intensity-functions of pigeon auditory primary afferents*. Hear Res, 1995. 83(1-2): p. 19-25.

[124]. Yates, G. K., G. A. Manley, and C. Koppl, *Rate-intensity functions in the emu auditory nerve*. J Acoust Soc Am, 2000. 107(4): p. 2143-54.

[125]. Koppl, C. and G. Yates, *Coding of sound pressure level in the barn owl's auditory nerve*. J Neurosci, 1999. 19(21): p. 9674-86.

[126]. Yates, G. K., *Basilar membrane nonlinearity and its influence on auditory nerve rate-intensity functions*. Hear Res, 1990. 50(1-2): p. 145-62.

[127]. Yates, G. K., I. M. Winter, and D. Robertson, *Basilar membrane nonlinearity determines auditory nerve rate-intensity functions and cochlear dynamic range*. Hear Res, 1990. 45(3): p. 203-19.

[128]. Winter, I. M., D. Robertson, and G. K. Yates, *Diversity of characteristic frequency rate-intensity functions in guinea pig auditory nerve fibres*. Hear Res, 1990. 45(3): p. 191-202.

[129]. Burns, E. M., *Developing a Catholic health care system*. Hosp Prog, 1976. 57(12): p. 48-54, 80.

[130]. Dorman, M. F., P. C. Loizou, and D. Rainey, *Speech intelligibility as a function of the number of channels of stimulation for signal processors using sine-wave and noise-band outputs*. J Acoust Soc Am, 1997. 102(4): p. 2403-11.

[131]. Shannon, R. V., F. G. Zeng, and J. Wygonski, *Speech recognition with altered spectral distribution of envelope cues*. J Acoust Soc Am, 1998. 104(4): p. 2467-76.

[132]. Fu, Q. J. and R. V. Shannon, *Recognition of spectrally degraded and frequency-shifted vowels in acoustic and electric hearing*. J Acoust Soc Am, 1999. 105(3): p. 1889-900.

[133]. Green, T., A. Faulkner, and S. Rosen, *Spectral and temporal cues to pitch in noise-excited vocoder simulations of continuous-interleaved-sampling cochlear implants*. J Acoust Soc Am, 2002. 112(5 Pt 1): p. 2155-64.

What is claimed is:

1. A method of generating frequency-modulated electrical pulse trains in a cochlear implant, comprising the steps of:
dividing data representing audio spanning a plurality of frequency bands into a plurality of bins associated with each of the frequency bands, each bin representing an energy level of the audio data within the frequency band within a period of time;
associating each frequency band with a phase probability that starts at an initial phase probability value, resets to a minimum phase probability value after a pulse is generated, and increases from the minimum phase probability value to a maximum phase probability value over a period of time;
for each bin, assigning a power probability as a normalized intensity for each bin, the normalized intensity being a number between a minimum power probability and a maximum power probability representing the energy level of the bin; and
for each bin, generating a pulse in an electrode associated with the frequency band associated with the bin when a random number generated is less than the power probability divided by the phase probability.

2. The method of claim 1, wherein a pulse rate in the electrode associated with the frequency band associated with the bin varies between zero pulses per second and a maximum pulses per second.

3. The method of claim 1, wherein the minimum power probability is 0.

4. The method of claim 1, wherein the maximum power probability is 1.

5. The method of claim 1, wherein the period of time is equal to one divided by a center frequency of the frequency band.

6. The method of claim 1, wherein the initial phase probability value is equal to the maximum phase probability value.

7. The method of claim 1, wherein the initial phase probability value is 1.

8. The method of claim 1, wherein the minimum phase probability value is 0.

9. The method of claim 1, wherein the maximum phase probability value is 1.

10. The method of claim 1, wherein the phase probability increases linearly.

11. The method of claim 1, wherein the phase probability increases according to a Gaussian function.

12. The method of claim 1, wherein the number of frequency bands corresponds to the number of electrodes in the cochlear implant.

13. The method of claim 1, wherein the random number generated is a random number between a minimum modified power probability and a maximum modified power probability; the minimum modified power probability defined as a smallest possible value of the power probability divided by the phase probability and the maximum modified power probability defined as a largest possible value of the power probability divided by the phase probability.

14. The method of claim 13, wherein the minimum modified power probability is 0.

15. The method of claim 13, wherein the maximum modified power probability is 1.

* * * * *